United States Patent
Ahira et al.

(10) Patent No.: US 9,952,193 B2
(45) Date of Patent: Apr. 24, 2018

(54) TEST STRIPS FOR VISUAL DIFFERENTIATION OF LIQUID MIXTURE COMPOSITION

(71) Applicant: FULLSPEED TECHNOLOGY INC., Burnaby (CA)

(72) Inventors: Gurdeep Ahira, Burnaby (CA); Paul Chi Hang Li, Coquitlam (CA); Abootaleb Sedighi, Burnaby (CA); Shuang Qiu, Guangzhou (CN); Chung Kay Michael Wong, Vancouver (CA); Wilson Ka Ho Chim, Burnaby (CA); Un I Cheang, Vancouver (CA)

(*) Notice: Subject to any disclaimer, the term of this patent is extended or adjusted under 35 U.S.C. 154(b) by 24 days.

(21) Appl. No.: 14/775,676

(22) PCT Filed: Mar. 14, 2014

(86) PCT No.: PCT/IB2014/001181
§ 371 (c)(1),
(2) Date: Sep. 12, 2015

(87) PCT Pub. No.: WO2014/140914
PCT Pub. Date: Sep. 18, 2014

(65) Prior Publication Data
US 2016/0178600 A1    Jun. 23, 2016

Related U.S. Application Data

(60) Provisional application No. 61/791,349, filed on Mar. 15, 2013.

(51) Int. Cl.
*G01N 21/75* (2006.01)
*G01N 33/28* (2006.01)
*G01N 31/22* (2006.01)
*G01N 21/78* (2006.01)
*G01N 21/77* (2006.01)

(52) U.S. Cl.
CPC ......... *G01N 33/2835* (2013.01); *G01N 21/78* (2013.01); *G01N 31/22* (2013.01); *G01N 33/2852* (2013.01); *G01N 2021/7759* (2013.01)

(58) Field of Classification Search
CPC .............. G01N 33/2835; G01N 21/78; G01N 33/2852; G01N 31/22; G01N 2021/7759
See application file for complete search history.

(56) References Cited

U.S. PATENT DOCUMENTS

2005/0158869 A1* 7/2005 Chandler .......... G01N 33/54366
436/164

OTHER PUBLICATIONS

Burgess et al, Encoding Complex Wettability Patterns in Chemically Functionalized 3D Photonic Crystals J. Am. Chem. Soc. 2011, 133, 12430-12432 (Year: 2011).*

(Continued)

*Primary Examiner* — Dennis White

(57) ABSTRACT

A test strip device exhibits visual changes, such as color changes, when there is a only slight difference in the composition of liquids such as gasoline, oil, ethanol and water. Such a slight liquid composition difference usually requires a sophisticated and expensive instrument to differentiate. The test strip consists of one and more than one inverse opal films deposited on a substrate and achieves this goal of differentiation in a simple, fast and energy-free manner.

20 Claims, 20 Drawing Sheets

(56) References Cited

OTHER PUBLICATIONS

Schroden et al,"Optical Properties of Inverse Opal Photonic Crystals" Chem. Mater. 2002, 14, 3305-3315 (Year: 2002).*
Burgess IB, Koay N, Raymond KP, Kolle M, Lončar M, Aizenberg J. Wetting in color: colorimetric differentiation of organic liquids with high selectivity. ACS Nano. 2012;6(2):1427-37.
Li, H., Wang, J., Yang, L. and Song, Y. (2008), Superoleophilic and Superhydrophobic Inverse Opals for Oil Sensors. Adv. Funct. Mater., 18: 3258-3264.
Burgess, Ian Bruce. 2012. Wetting in Color. Doctoral dissertation, Harvard University.
Abootaleb Sedighi, Shuang Qiu, Michael C. K. Wong, and Paul C. H. Li, Dip-in Indicators for Visual Differentiation of Fuel Mixtures Based on Wettability of Fluoroalkylchlorosilane-Coated Inverse Opal Films, ACS Appl. Mater. Interfaces, 2015, 7 (51), pp 28387-28392
Benjamin Hatton, Lidiya Mishchenko, Stan Davis, Kenneth H. Sandhage, Joanna Aizenberg, Assembly of large-area, highly ordered, crack-free inverse opal films, Proceedings of the National Academy of Sciences Jun. 2010, 107 (23) 10354-10359.
Benjamin Hatton, Lidiya Mishchenko, Stan Davis, Kenneth H. Sandhage, Joanna Aizenberg, Assembly of large-area, highly ordered, crack-free inverse opal films, Proceedings of the National Academy of Sciences Jun. 2010, 107 (23) 10354-10359, Supporting Information (SI).

* cited by examiner (a)

Water on C18 IOF, Contact angle = 106°, not-

(b)

(c)

95% ethanol on C18 IOF, Contact angle = 45°, wetted

(d)

Toluene on C18 IOF, Contact angle = 26°, wetted

(e)

TEST STRIPS FOR VISUAL DIFFERENTIATION OF LIQUID MIXTURE COMPOSITION

FIELD OF THE INVENTION

The present invention relates to a test strip for differentiating between compositions of liquids, and in particular to a test strip for displaying visual changes, such as color changes, in the presence of liquids of different compositions.

BACKGROUND OF THE INVENTION

Currently, there are many tests available to analyze their composition. These include the tests for viscosity, oxidation products, nitration products, glycol, soot, water, total acid number, elemental analysis, total base number, and particle count. However, these chemical tests are tedious methods for analysis.

SUMMARY OF THE INVENTION

Known chemical tests for analyzing the composition of petroleum fuels and oils are tedious, and they are not colorimetric tests that can be easily adapted in the test strip format.

The present invention is a test strip that differentiates between the compositions of various liquid mixtures, such as gasoline/oil and gasoline/ethanol mixtures of very close wettabilities. The strip consists of a substrate with several inverse opal films (IOFs) deposited on it. The test strip achieves visual means for differentiating between compositions of liquids, and in particular the test strip displays visual changes, such as color changes, in the presence of liquids of different compositions.

There are methods other than chemical for testing compositions of various liquid mixtures. The present invention utilizes the test for liquid wettability using inverse opal film (IOF). The IOF, which consists of a regular arrangement of spherical void spaces surrounded by solid walls, has demonstrated its functionalities in a broad range of applications such as power sources [1-3], photonics [4-6], catalysis [7-8] as well as sorption and controlled release of drugs [9-10]. However, their exceptional potentials are in sensing applications [11], and they have been utilized in various optical [12-15], and electrochemical [16-17] sensors developed in the last decade. Sensing can benefit from several properties of IOF, including their highly accessible surface, their nanostructured features (e.g. nanopores) and most prominently their structural color. The color, also called iridescence color, depends on the viewing angle. The origin of the color is derived from light scattering and interference rather than absorption, and the color is sensitive to the structural changes of the nanomaterials. The structural color arises from the refractive index difference between the silica walls of the nanopores and air which occupies the empty pores and the color can be changed when the empty pores are filled with liquids [18]. Therefore, this color can be readily tuned by changing various aspects of the structure (e.g. size, shape, aspect ratio and refractive index) and, thus, the IOF appears to be a promising tool in the chemical sensing [18].

Synthesis of the IOF requires the assembly of the colloidal particles into the colloidal crystal template (CCT) using different approaches such as sedimentation, centrifugation and vertical deposition [19]. Depends on the synthesis method, various defects are provoked in the CCT structure [20]. While most of the IOF applications can tolerate the defects, the optical sensors are highly affected by the defects [11]. Hatton et al. in 2010 developed a novel co-assembly approach to create large-area crack-free IOF [21]. The IOFs made via the new method showed a great potential for colorimetric differentiation of closely related fluids [22-24]. In these applications, the hydrophilic silica surfaces of the IOF were rendered hydrophobic by patterning the surfaces with alkylchlorosilanes. Depending on their surface tensions, different liquids fill different fractions of the IOF pores which, therefore, results in different colors [23]. Using this technique colorimetric differentiation of ethanol/water mixtures with ratio difference of 2.5% was achieved [23]. However differentiation of liquids with closer surface tensions (e.g. linear alkanes with close chain lengths) require more complicated approaches such as comparison of colorimetric wetting patterns produced by liquids in an array of IOFs or comparison of the drying times of the IOFs following to the filling by different liquids [24]. These complicated approaches have not succeeded in differentiate between different composition of organic liquid mixtures.

With this invention we have successfully created visual test strips based on the IOF to differentiate various liquid mixtures, such as gasoline/oil and gasoline/ethanol mixtures of very close wettabilities. These mixtures are routinely used as fuels in 2-stroke engines (gasoline/oil mixtures) and 4-stroke engines (gasoline/ethanol) and the liquid composition highly affect the engine performance as well as its endurance. The test strips that may provide colorimetric changes are aimed to be simple-to-test, easy-to-read, robust and selective enough to differentiate closely-related liquids. In order to meet these criteria, a binary fashion of "wetted" vs. "non-wetted" is attributed to the IOF as it is immersed in different mixtures. Since the iridescence color of IOF arises from the refractive index difference between the walls of the nanopores and air which occupies the empty pores, the structural color disappears when the IOF is wetted because a liquid infiltrates in the IOF porous structure. The disappearance of the color is due to the fact that the refractive index of the liquid matches with that of the pore wall. The IOF is "non-wetted" if it resists the liquid infiltration and, thus, retains the structural color. We investigate different factors (e.g. intrinsic contact angle, pore neck angle, pore packing ratio and film thickness) that govern the wettability of the IOF. A combined tuning of these factors is used to prepare IOFs capable of differentiating different liquids and different liquid mixtures, such as gasoline/oil mixtures and gasoline/ethanol mixtures.

The test strip consists of a substrate 10 with several inverse opal films (IOFs) deposited on it.

The test is based on liquid wettability, which is the degree to which a liquid will spread on a surface. If the liquid does not spread, it does not wet the surface. If the liquid spreads, it is considered to wet the surface. Shown in FIG. 1 are two IOFs 12 filled with air and not wetted by liquids, and three IOFs 13 wetted by liquids that filled the nanopores.

This strip works on liquids of different surface tensions, like a litmus paper that works on acids and bases of different pH values. For example, when the litmus paper is placed in an acidic solution, the paper turns red, and when the litmus paper is placed in a basic solution, a blue color is resulted. This color change is based on chemical reactions. The test strip is made to differentiate between different gasoline and oil mixtures, and different gasoline and ethanol mixtures based on liquid wettability. FIG. 2 shows a region of the test strip, in which there is a test spot of IOF 12 in blue on a substrate 10. When this blue spot is in a liquid that does not wet the surface (i.e. oil), the blue color will not disappear.

On the other hand, when this blue spot is in a liquid that wets the surface (i.e. gasoline), the blue color disappears. This differential color change is caused by the wettability of gasoline, but non-wettability of oil.

This device is important to the chemical industry for differentiating between various liquid mixtures of very close wettabilities. For example, a chain saw has a 2-stroke or 2-cycle engine. This engine requires a proper mixture of gasoline and oil to work. Gasoline is used for providing the energy and oil serves as the lubricant. However, if the mixture contains too much oil, the engine would not have enough power. On the other hand, if the mixture contains too much gasoline, the engine wouldn't have enough lubricant to protect the engine parts. Therefore, companies or manufacturers that make this type of gasoline/oil product must make sure their products have the right ratio of gasoline to oil. Gasoline to oil ratios can range between 16:1 to 80:1. The common ratios would be 50:1, 40:1, 32:1, 25:1, 20:1 and 16:1. However, the known methods for testing the quality of the product require a large amount of time and work. Therefore, it would be advantageous to have something similar to a litmus paper that can readily test the product and have the test results in a few seconds.

According to one aspect of the invention, the test strip is adapted for differentiating between compositions of liquids, such as displaying visual changes, as and in particular displaying color changes, in the presence of liquids of different compositions, is based upon a first substrate. At least one inverse opal film is deposited on the first substrate. And at least one chemical coating is deposited inside the pores of the at least one inverse opal film.

According to another embodiment of the invention, the first substrate of the test strip is silicon, quartz, or glass.

According to another embodiment of the invention, the inverse opal film of the test strip is made of silica, zirconia or titania.

According to another embodiment of the invention, the chemical coating of the test strip is a silane. The silane is optionally a fluorosilane. The fluorosilane is optionally of a different chain lengths from about 3 to about 17.

According to another embodiment of the invention, the test strip for differentiating between compositions of liquids is based upon a first substrate, and at least one inverse opal film deposited on at least one second substrate. At least one IOF is deposited on at least one second substrate is mounted on the first substrate. And at least one chemical coating is deposited in the pores of the at least one inverse opal film. Optionally, the first substrate of the test strip is silicon, quartz, glass, plastic or paper. Optionally, the second substrate of the test strip is silicon, quartz, or glass. Optionally, the inverse opal film of the test strip is made of silica, zirconia or titania. The chemical coating of the test strip may be a silane, and the silane may be a fluorosilane. When the silane is a fluorosilane, the fluorosilane is optionally of different chain lengths from about 3 to about 17.

According to another embodiment of the invention, test strip is further adapted to differentiate at least two liquids. Optionally, at least one of the two liquids differentiated by the test strip is a liquid mixture.

According to one embodiment of the invention, the liquid mixture differentiated by the test strip is water and ethanol. The test strip of the invention is optionally adapted to differentiate water and ethanol mixtures of any ratio. By example and without limitation, the ratio of the water and ethanol mixture differentiated by the test strip is in the range of 5:95 to 50:50.

According to another embodiment of the invention, test strip is further adapted to differentiate liquid mixtures of gasoline and engine oil. The test strip of the invention is optionally adapted to differentiate liquid mixtures of any ratio of gasoline and engine oil. By example and without limitation, the ratio of the gasoline and engine oil mixture differentiated by the test strip is one of 50:1, 40:1, 32:1, 25:1, 20:1, or 16:1.

According to another embodiment of the invention, test strip is further adapted to differentiate liquid mixtures of gasoline and ethanol. The test strip of the invention is optionally adapted to differentiate liquid mixtures of any ratio of gasoline and ethanol. By example and without limitation, the ratio of the gasoline and ethanol mixture differentiated by the test strip is one of 95:5, 90:10, or 85:15.

Other aspects of the invention are detailed herein.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF PREFERRED EMBODIMENT

As required, a detailed illustrative embodiment of the present protective enclosure is disclosed herein. However, techniques, systems and operating structures in accordance with the present protective enclosure may be embodied in a wide variety of forms and modes, some of which may be quite different from those in the disclosed embodiment. Consequently, the specific structural and functional details disclosed herein are merely representative, yet in that regard, they are deemed to afford the best embodiment for purposes of disclosure and to provide a basis for the claims herein which define the scope of the present protective enclosure. The following presents a detailed description of an illustrative embodiment (as well as some alternative embodiments) of the present protective enclosure.

In the Figures, like numerals indicate like elements.

Figure 1:
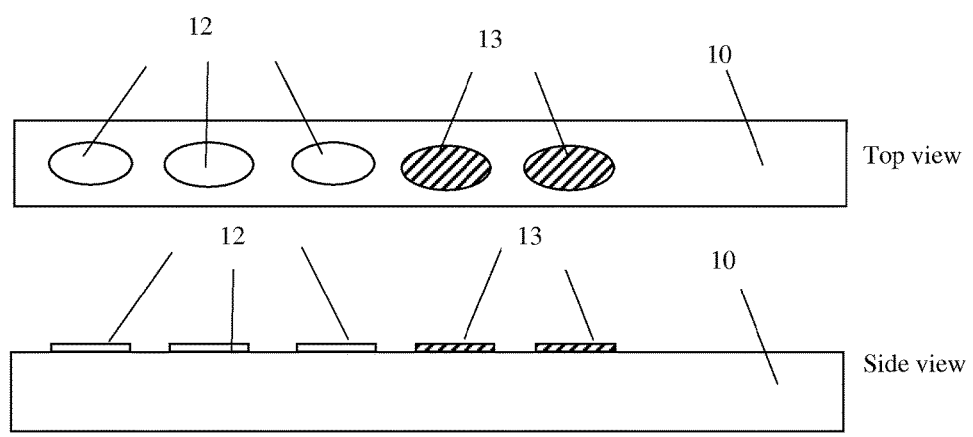
FIG. 1: A test strip consists of a substrate on which one or more than one inverse opal film (IOF) is deposited. An example of a test strip consisting of 5 IOFs was shown, with 2 wetted (W) and 3 not wetted (N).
Figure 2:
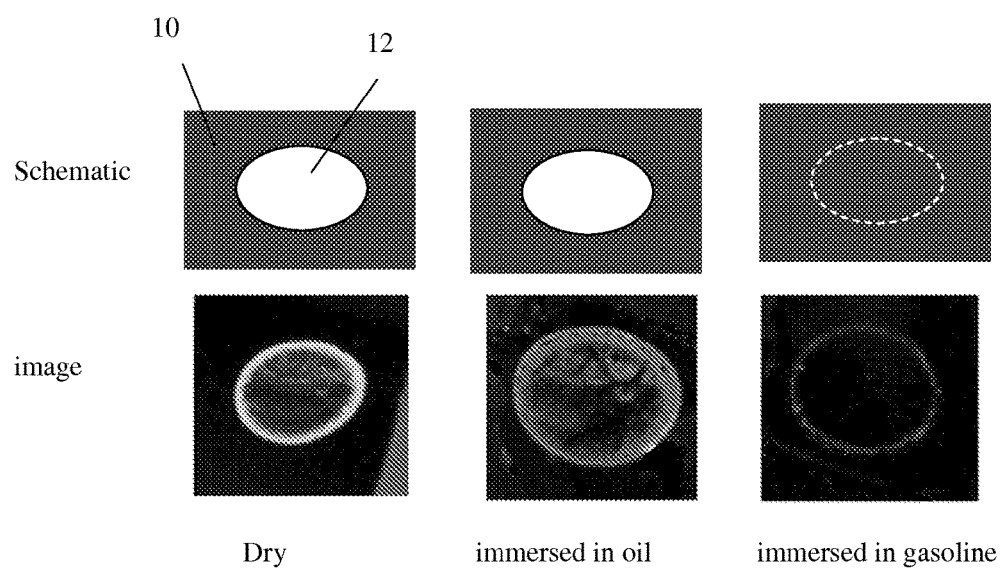
FIG. 2: Schematic diagrams and images of the test results of an inverse opal film (IOF) constructed using the spotting method on a silicon substrate. The left ones show the dry IOF spot in blue before testing with a liquid. The middle ones depict the test strip when it was immersed in oil in which no wetting and no disappearance of the blue spot occurred. The right ones show the wetting and color disappearance of the IOF spot when it was immersed in gasoline.
Figure 3:
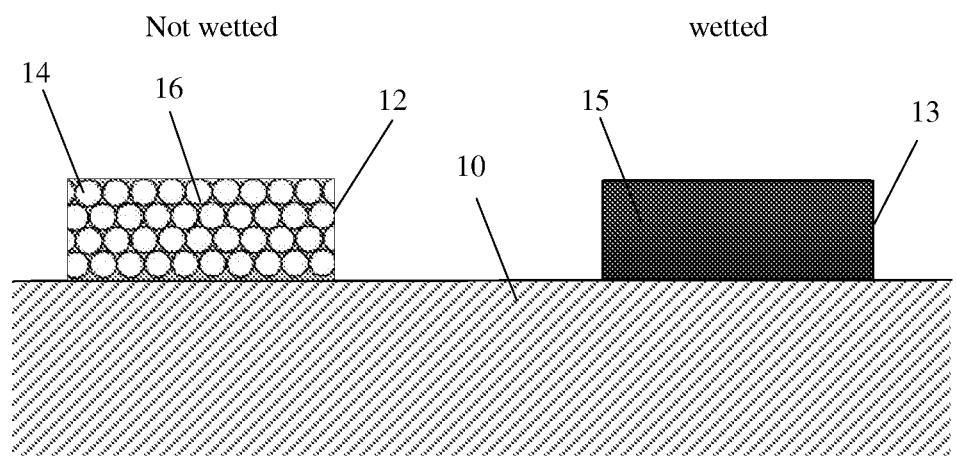
FIG. 3: A region of a test strip that shows the not-to-scale drawing of two inverse opal films (IOFs) deposited on the substrate. The open circles represent empty nanopores filled with air. These nanopores will be coated by a material that alters the wettability of a liquid on the IOF. The grey circles represent the nanopores filled with a liquid.

FIG. 1 illustrates one embodiment of the invention for a test strip for differentiating between various liquid mixtures of very close wettabilities. The test strip is made by synthesizing an inverse opal films (IOF) 12 on a substrate 10, such as silicon, quartz and glass (FIG. 3). There are 3 steps in this synthesis process. First, polymeric nanospheres, which form a close packing on the substrate, are used as a template with the interstitial space filled with a solid material. This material can be made of silica, titania or zirconia. Second, the polymeric template will be thermally decomposed and vanishes as gaseous products, leaving the nanopores 14 behind, forming an inverse opal film (IOF). Third, a silane vapor is used to fill the inner surface of nanopores within the IOF and form a coating 16.

In the first step, polymethylmethacrylate (PMMA) nanospheres were mixed with an acidic solution of tetraethoxysilane (TEOS) to form a PMMA/TEOS colloid. This liquid colloid was applied to surface of a clean silicon surface using different methods, namely evaporation method, pulling method, pipetting method, microfluidic method, cover slip method, dripping method, and spotting method. A close packing of the PMMA nanospheres was allowed to self-assemble on the silicon surface. The TEOS act like a filler agent that occupied the space between the PMMA nanospheres. TEOS would gel into silica ($SiO_2$) over time.

In the second step, the silicon substrate was gradually heated up to 500° C. At this temperature, the PMMA would decompose and evaporate and the silica would calcinate and harden. This calcination step left behind a highly uniform porous network called the inverse opal film (IOF). In the third step, the inner surface of nanopores 14 in the IOF would be functionalized with a silane compound to alter the wettability of the IOF nanopores by liquids. When wetted, the nanopores was filled with liquid 15. If not wetted, the nanopores are filled with air 13.

For the evaporation method, the PMMA/TEOS colloid was allowed to evaporate, creating a retracting thin film on the substrate. For the pulling method, the substrate was slowly pulled up vertically from the PMMA/TEOS colloid, leaving a thin film behind on the substrate. For the pipetting method, the silicon substrate was completely covered with the PMMA/TEOS colloid by pipetting the solution on it. For the microfluidic method, a microfluidic chip was sealed to the silicon substrate and the PMMA/TEOS colloid was introduced into the microchannels wetting the surface of the silicon substrate. For the cover slip method, a cover slip was used to apply a thin layer of the PMMA/TEOS colloid on the silicon surface. For the dripping method, the PMMA/TEOS colloid was applied to the top of the silicon substrate using a micropipette and the colloid was allowed to drip down onto the substrate. For the spotting method, PMMA/TEOS colloid was spotted on the substrate, and this produced a circular blue spot.

The spotting method was chosen to be an adequate method because this created a well-defined IOF spot instead of a larger IOF area without a defined region obtained by the pipetting, dripping and cover slip methods. This spotting method was easy and fast to prepare and it required only 1 µL of colloid. However, this method would not synthesize IOF with a large area, highly ordered, crack-free region. To achieve a large area IOF, the evaporation method was adopted.

Materials

Polymethylmethacrylate (PMMA) nanospheres (Polysperex™) with diameters of 318±12 nm and 450 nm, suspended in deionized (DI) water (1% w/v) were purchased from Phosphorex Inc. (Hopkinton, Mass.). Tetraethylorthosilicate (TEOS), 3-aminopropyltriethoxysilane (APTES), chlorotrimethylsilane (TMS), trichloro(hexyl)silane (C6), (3,3,3-trifluoropropyl)trichlorosilane (3FS) and (1H,1H,2H,2H-perfluorooctyl)trichlorosilanesilane (13FS), were obtained from Sigma-Aldrich. Dimethyldichlorosilane or repel silane (RS) was obtained from GE Healthcare (Uppsala, Sweden). Chloro(dimethyl)octadecylsilane (C18), triphenylchlorosilane (TPS), (nonafluorohexyl)trichlorosilane (9FS), heptadecafluoro(1,1,2,2-tetrahydrodecyl)trichlorosilane (17FS) and perfluorododecyl(1H,1H,2H,2H-)triethoxysilane (25FS) was purchased from Gelest Inc. (Morrisville, Pa.). Zirconium acetate, ethanol, methanol, and toluene were also purchased.

Two-stroke motor oil was purchased from Castrol, and the pure gasoline containing no ethanol (octane number 94) was obtained from a local Chevron gas station. Clear polystyrene (PS) cuvettes were purchased from Fisherbrand.

Support Substrates

Silicon (Si) wafers (10 cm diameter×1 mm) were purchased from Cemat Silicon (Warsaw, Poland); glass slides (3 cm×4.5 cm×1 mm) and quartz slides (3 cm×4.5 cm×1 mm) were from GM Associate (Oakland, Calif.). They were cut into 4.5 cm×0.8 cm strips using a diamond cutter. These strips were cleaned in the piranha solution (70% of concentrated sulfuric acid and 30% of hydrogen peroxide) for 15 min. the strips were rinsed with DI water and blow-dried using nitrogen gas.

Silica IOF Synthesis by Spotting Method

The 0.010M hydrochloric acid was prepared by mixing 120 µL water with 1 µL hydrochloric acid (36.5-38.0%). Then, tetrathoxysilane (TEOS, 98%) was mixed with 0.010M HCl and 95% ethanol at a ratio of 1:1:1.5 (by weight) to produce acidic TEOS.

The PMMA stock colloid was sonicated at room temperature for 20 minutes. After sonication, PMMA colloid and acidic TEOS were mixed at a ratio of 10:1 i.e. 166.7 µL PMMA and 16.7 µL acidic TEOS.

A micro-pipettor was used to spot the PMMA/TEOS solutions (1 µL) onto the glass and silicon substrate.

Silica IOF Synthesis by Evaporation Method

HCl (0.01 M, 252 µl), 270 µl of TEOS and 480 µl of anhydrous ethanol (EtOH) were mixed in a glass vial in order to prepare 1 ml of the standard TEOS solutions (1:1:1.5 ratios by weight of HCl:TEOS:EtOH). The solution was stirred at 200 rpm for 1 hour.

Figure 4:
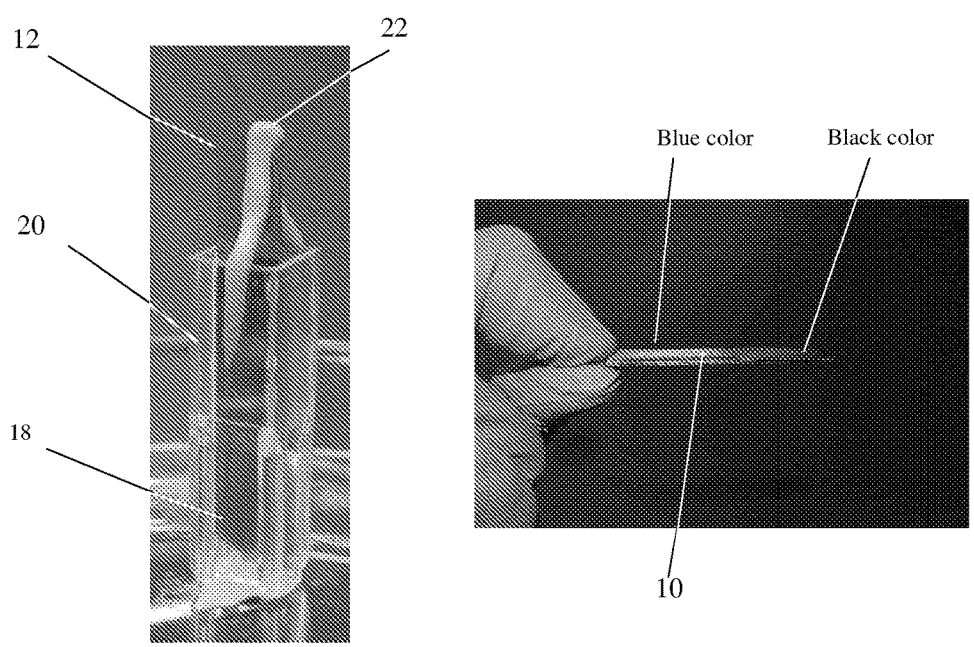
FIG. 4: The inverse opal film (IOF) constructed on a silicon substrate using the evaporation method. The left image shows the silicon strip immersed in the PMMA/TEOS colloid placed inside a cuvette. The right image shows the silica IOF in blue color formed on the silicon strip after calcination.

In order to homogenize the stock colloids of PMMA, they were sonicated for 30 min. An aliquot of PMMA colloid (100-400 µL) and TEOS solution (10-40 µL) were mixed with 2 mL of deionized (DI) water to form a PMMA/TEOS colloid 18 and put in cuvette 20. The cuvette was then capped and sonicated for an hour. After sonication, the cleaned Si strip 10 was suspended vertically in cuvette 20 and fixed in position using a paste 22 (FIG. 4). The procedure was repeated for other aliquots of PMMA colloid and TEOS solution. All these cuvettes were placed in an oven and the TEOS/PMMA films were allowed to deposit on the strip surfaces as the solution evaporated at 58° C. for 48 hours. In order to avoid variation of humidity between different batches, a constant number of cuvettes (12 cuvettes) were always placed in the oven. After all the solution in the cuvettes dried out, the cuvettes were removed from the oven and the strips, with the composite film deposited on their surface, were placed back into the oven. The oven temperature was ramped up to 500° C. over 4 hours, held at that temperature for 2 hours and ramped down to room temperature over 1 hour. After decomposition of the PMMA nanospheres from the deposited film by high temperature, the IOFs were formed, and they were placed in the piranha solution at 85° C. for an hour for cleaning and subsequently submerged in DI water for 4 hours.

Zirconia IOF Synthesis by Spotting Method

Acidic zirconium acetate was prepared by mixing 1.3 µL zirconium acetate (solution in dilute acetic acid, 15-16% Zr)

and 8.7 µL methanol in a ratio of 1:7, unless otherwise stated. Meanwhile, the PMMA stock colloid was sonicated at room temperature for 20 minutes. After sonication, 1 µL of the acidic zirconium acetate solution was mixed with 9 µL of PMMA stock colloid in a ratio of 1:9, unless otherwise stated.

A micro-pipettor was used to spot the PMMA/zirconium acetate colloid (1 µL) onto the glass and silicon strips.

Calcination

After the PMMA/TEOS or PMMA/zirconium acetate colloid was dried, the inverse opal film template was put in the oven for thermal decomposition. Meanwhile, the silica or zirconia was calcinated and hardened. The oven (Vulcan3-550) was used, and the temperature was set to increase by 2.0° C./min to 500° C., and hold for 2 h.

Chemical Vapor Deposition

Figure 5:
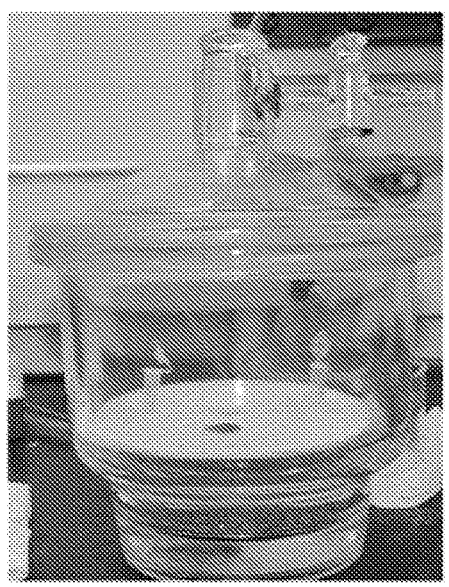
FIG. 5: A vacuum desiccator was used to conduct chemical vapour deposition of a silane into the nanopores of the IOF placed inside. The silane solution was placed in two vials and the IOF strip was placed in the middle.
Figure 5:
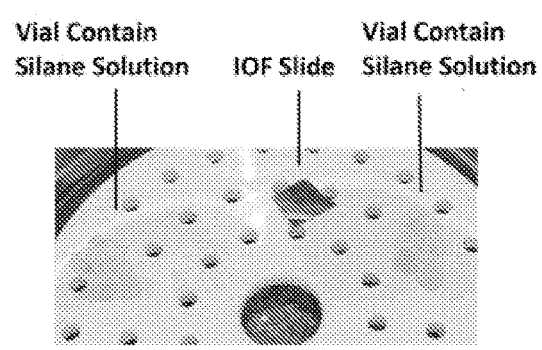

Several silanes were used to deposit the IOF by the chemical vapour deposition method, and these chemicals were tabulated in Table 1. Two portions of 200 µL of repel-silane (RS) solution were put into two 1.5-mL vials and they were placed into a desiccator. After calcination, the substrate was placed in the middle of the desiccator with the inverse opal film facing the repel-silane solution (FIG. 5). Then, the desiccator was put under vacuum for 24 hours. After one day of chemical vapour deposition, the pressure in the desiccator was released. Then, the lid was opened to retrieve the functionalized IOF strips.

In the application of fluoroalkylchlorosilanes, two small and uncapped vials each containing 60 µL of the solutions were placed inside the chambers and the IOFs were exposed to the chemical vapours for 24 hours. Patterning of the IOF surface with multiple chemicals was performed by mixing the chemicals with various volume ratios in each vial. Following the chemical patterning, the IOFs were baked at 150° C. for 20 min.

Removal of Deposited Alkylsilanes

In order to replace the previous silane deposited on the IOF surfaces by a new silane, the old silane was first stripped from the IOF surface using an oxygen plasma. The IOF strips were exposed to oxygen plasma (100 W, 15 sccm $O_2$) for 15 min in an Etchlab 200 instrument (Sentech, Bethesda, Md.). The stripped IOFs were then cleaned in the piranha solution (85° C.) for 1 hour and DI water for 4 hours. The chemical vapor deposition of the new silane was performed according to the procedure described in the preceding section.

Wettability Tests

In a 60-ml glass vial, various volumes of oil was added to pure gasoline in order to prepare mixtures with gasoline:oil with the ratios of 16:1, 20:1, 25:1, 32:1, 40:1, 50:1. Anhydrous ethanol was also added to pure gasoline in order to prepare E5 (5% ethanol in gasoline) and E10 (10% ethanol in gasoline). Prior to the wettability tests, the IOF strips were washed with anhydrous ethanol and dried with compressed air. The IOFs were immersed in the liquid mixtures and kept at a slightly tilted angle for 10 s (this time was enough to ensure no change in the wettability occurs afterwards). Photographs were taken using a cell phone camera.

EXAMPLES

Figure 6:
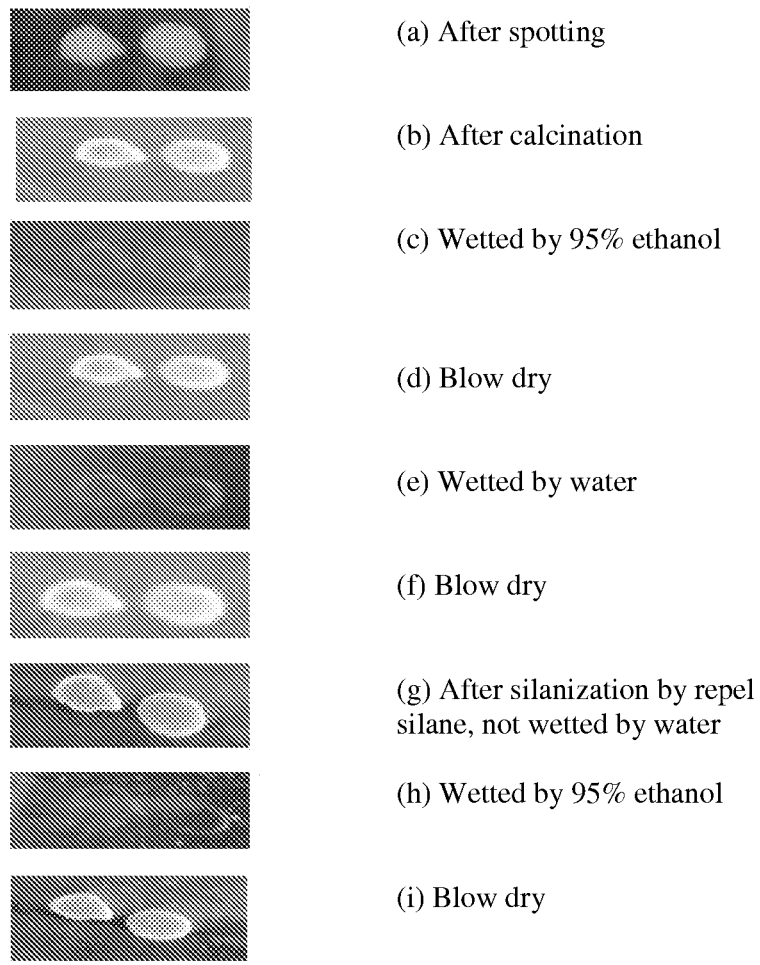
FIG. 6: A series of events occurring to the two IOFs made by the spotting method on a silicon strip. (a) dried spots after colloid deposition, (b) blue IOF spots after calcination, (c) disappearance of the blue color after wetting by 95% ethanol, (d) recovery of the blue spots after blown dry by nitrogen gas, (e) disappearance of the blue color again after wetting by water, (f) recovery of the blue color after blown dry by nitrogen gas, (g) after silanization of the IOF by dimethyldichlorosilane (RS), the two spots were not wetted by water any more, (h) the silanized IOF spots were wetted by 95% ethanol, losing the blue color, (i) recovery of the blue color after blown dry by nitrogen gas.

Test Results of Silica IOF Prepared by the Spotting Method on Silicon and Glass Substrates Two IOF spots were created and tested, see FIG. 6. After obtaining the dried spots after deposition of the TEOS/PMMA colloid, they were calcinated at 500° C. to produce the blue spots which were the silica IOF. The IOF spots were wetted by 95% ethanol, and so the blue color disappeared. The blue color was recovered after ethanol removal from the spots when blown dry by nitrogen gas. Another test using water also showed disappearance of the blue color because of wetting by water. The blue color reappeared after blown dry to remove water by nitrogen gas. Thereafter, the IOF was functionalized due to silanization by dimethyldichlorosilane or repel silane (RS). Then, the two spots were not wetted by water any more, but were wetted by 95% ethanol, losing the blue color.

Figure 7:
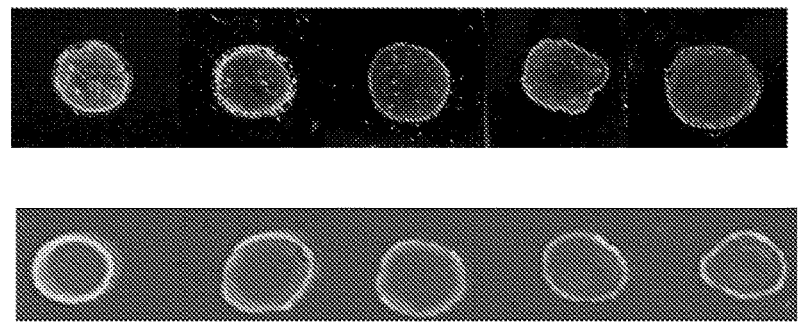
FIG. 7: Five spots have been created on the silicon strip. The contrast of the blue color of the IOF spots made on silicon substrate (top) is better than those spots made on a glass substrate even though a black paper was placed underneath the glass strip for easy visualization.

Multiple spots were created on the silicon strip as shown in FIG. 7. The contrast of the blue color of the IOF spots made on silicon substrate was superior to those made on a glass strip even though a piece of black paper was placed underneath the glass for easy visualization.

Figure 8:
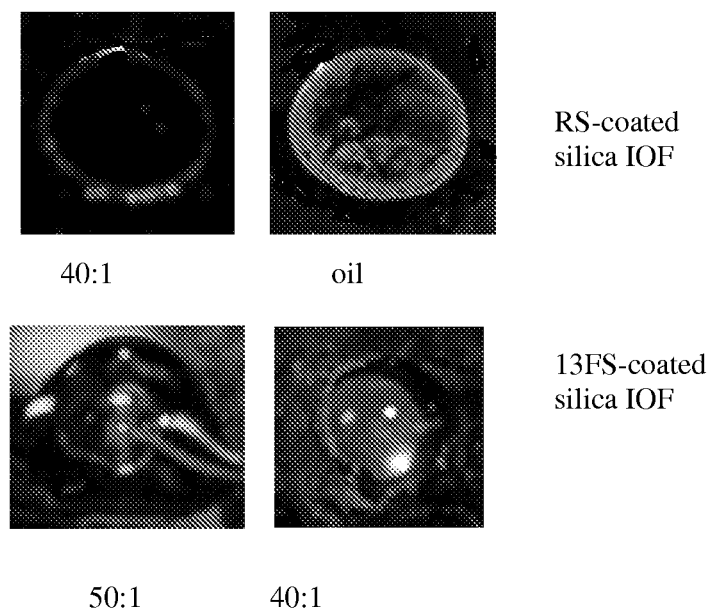
FIG. 8: The blue color with RS was removed by the 40:1 mixture, but was not removed by oil, and so RS can be used to differentiate between oil and the 40:1 mixture. On the other hand, the blue color with 13FS did not get removed by 40:1 mixture, but removed by the 50:1 mixture. Therefore, 13FS can be used to differentiate between 50:1 and 40:1 mixtures.

More liquids were employed for testing liquid wettability on these IOF spots made on silicon strips. Water, 95% ethanol, toluene, gasoline, 50 parts of gasoline to 1 part of oil (50:1), 40 parts of gasoline to 1 part of oil (40:1), 1 part of gasoline to 1 part of oil (1:1) and pure oil were used to test on different blue spots that consisted of the IOF deposited with a different silane. The results are shown in Table 2. The color of all the IOF spots was not removed by water because water did not wet the IOFs. However, the oil removed the blue color on all of the spots except those treated by RS and 13FS. The blue color with RS got removed by the 40:1 mixture, but did not get removed by oil. The blue color with 13FS did not get removed by the 40:1 mixture, but removed by the 50:1 mixture. Therefore, RS can be used to differentiate between oil and the 40:1 mixture, and 13FS can be used to differentiate between the 50:1 and 40:1 mixtures (FIG. 8).

Figure 9:
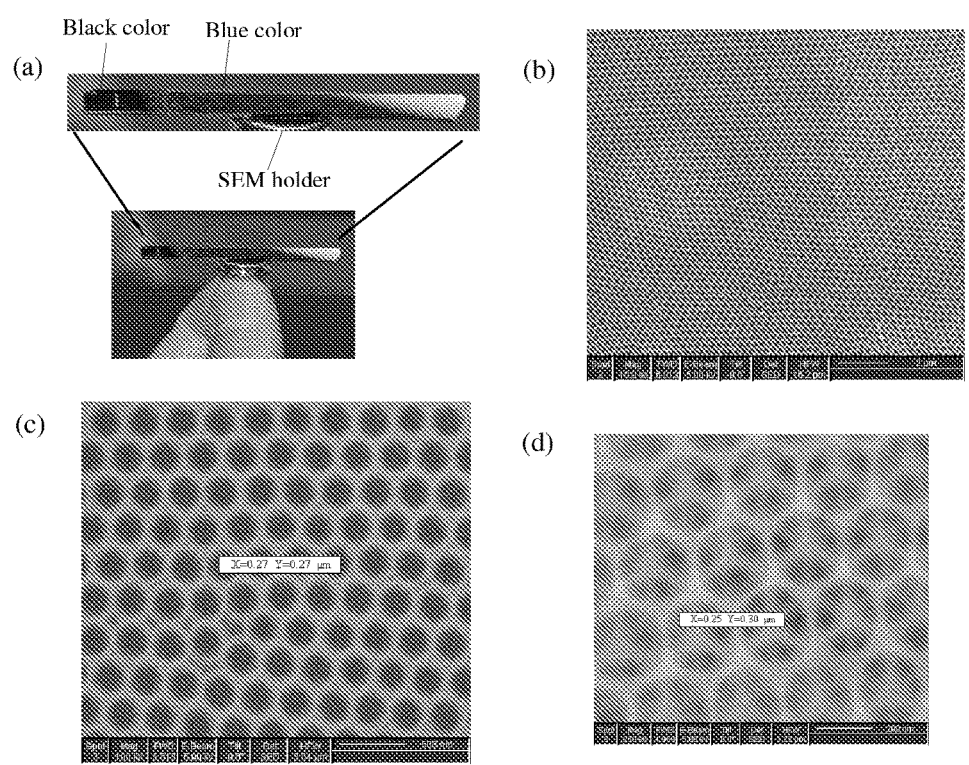
FIG. 9: An IOF made by the evaporation method. (a) the blue colored IOF mounted on a scanning electron micrograph (SEM) holder, with the inset showing the large uniform blue region of the IOF, (b) SEM image of the IOF (scale bar 2 μm), (c) SEM image of the IOF (scale bar 500 nm), (e) SEM image of the IOF (scale bar 200 nm).

On Silicon Substrates: Test Results of Silica IOF Prepared by the Evaporation Method In order to create an IOF to cover an area of a larger extent, the evaporation method was used. After obtaining the dry film after deposition, it was calcinated at 500° C. to produce the blue colored silica IOF on silicon substrate (FIG. 9). Scanning electron micrograph (SEM) of the IOF was performed. The circular dark regions represent the nanopores while the white region represents the silica wall. An estimated pore size of 300 nm or 0.30 nm was determined in FIG. 9d. It was also clear to see the silica wall of underneath layer in the SEM image at a higher magnification. It is this regular arrangement of nanopores in multiple layers that produces the structural color of blue.

Figure 10:
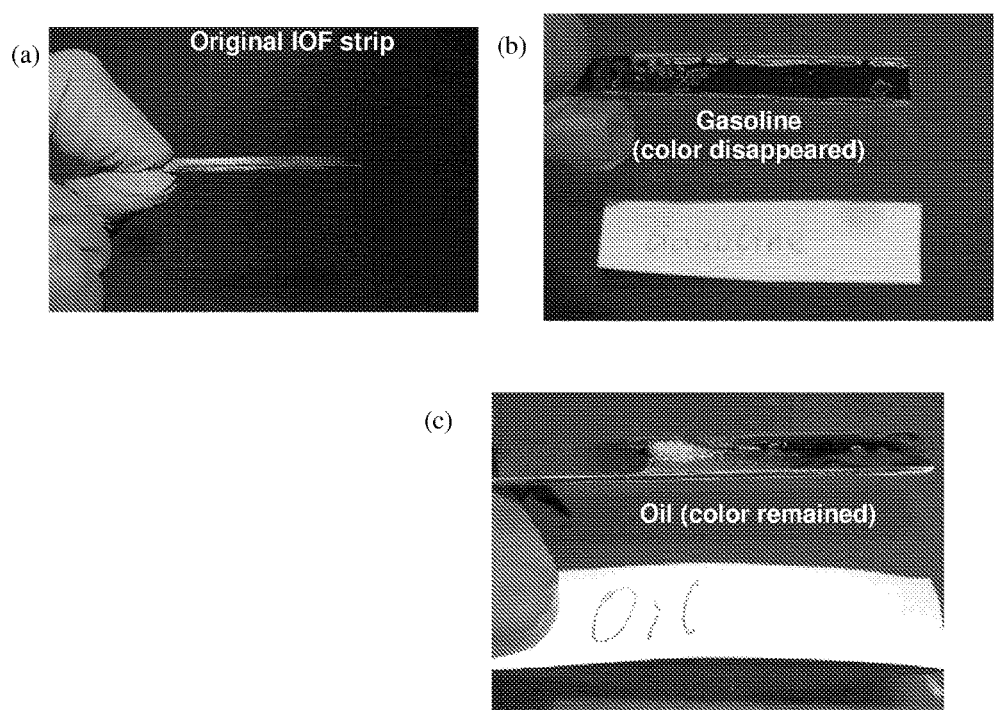
FIG. 10: Tests performed on the IOF silanized with dimethyldichlorosilane or repel silane (RS): (a) dry IOF shown; (b) when gasoline was pipetted onto it, it was wetted and the blue color disappeared; (c) when pure oil was pipetted onto the IOF, the blue color remained.

After the IOF was silanized, it was employed for testing with organic liquids. FIG. 10 shows the IOF silanized with dimethyldichlorosilane or repel silane (RS). FIG. 10a shows the original IOF strip. When gasoline was pipetted onto it, it was wetted and the blue color disappeared (FIG. 10b). When pure oil was pipetted onto the IOF strip, the blue color remained (FIG. 10c).

Figure 11:
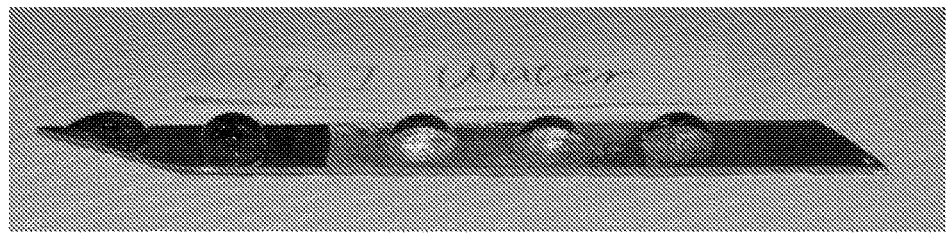
FIG. 11: Contact angles of liquid drops on the IOF silanized with C18. (a) several water drops on the silanized IOF produced a contact angle of 106°. They did not wet the IOF and the color remained. (b) schematic diagram showing the 3 droplet areas have the same color as the surrounding IOF, (c) several drops of 95% ethanol on the silanized IOF produced a contact angle of 45°. They wetted the IOF and the color disappeared. (d) several toluene drops on the silanized IOF produced a contact angle of 26°. They wetted the IOF and the color disappeared. (e) schematic diagram showing the 3 droplet areas were blackened as compared to the surrounding colored IOF.
Figure 11:
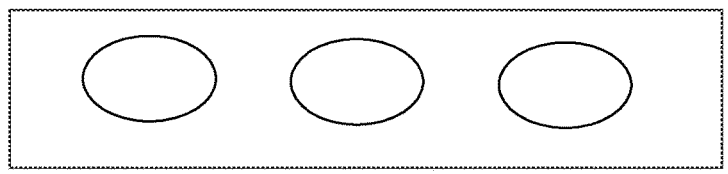
Figure 11:
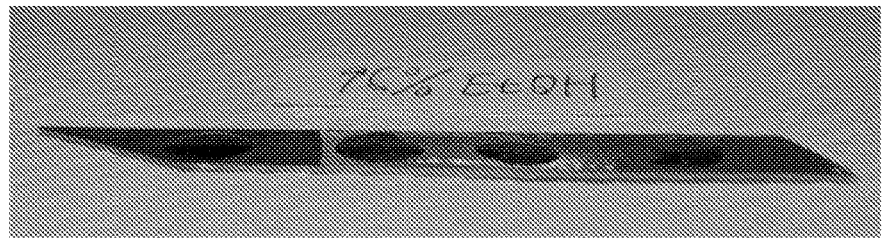
Figure 11:
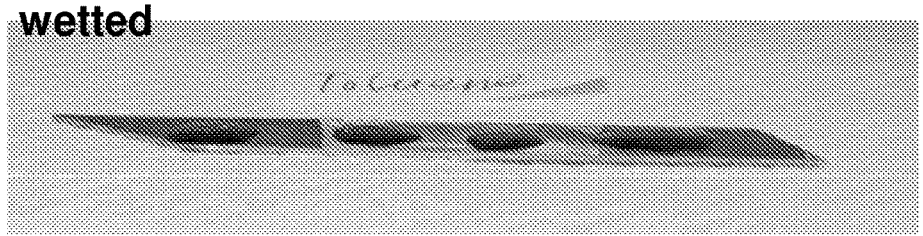
Figure 11:
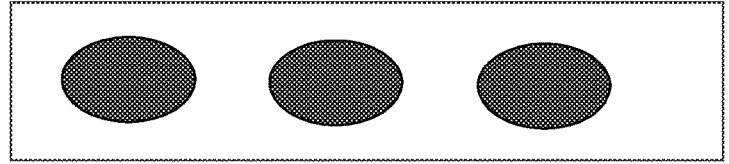

The wetting and non-wetting of liquids on IOF are governed by the contact angles of the liquid drops formed on the surface. Contact angle measurement of liquid drops placed on the IOF silanized with C18 was conducted. FIG. 11a showed several water drops placed on the silanized IOF did not wet the IOF and the color remained (contact angle is 106°). Note the iridescence color seen by the refraction of the hemispherical liquid drop that act like a lens. FIG. 11b shows a schematic of the 3 circles that didn't alter the IOF color on the strip. FIG. 11c showed several drops of 95% ethanol wetted the silanized IOF, causing the disappearance of the blue color (contact angle=45°). FIG. 11d showed several toluene drops also wetted the silanized IOF, causing the blue color to disappear (contact angle=26°). FIG. 11e shows the schematic of 3 dark circles because of liquid wetting.

Figure 12:
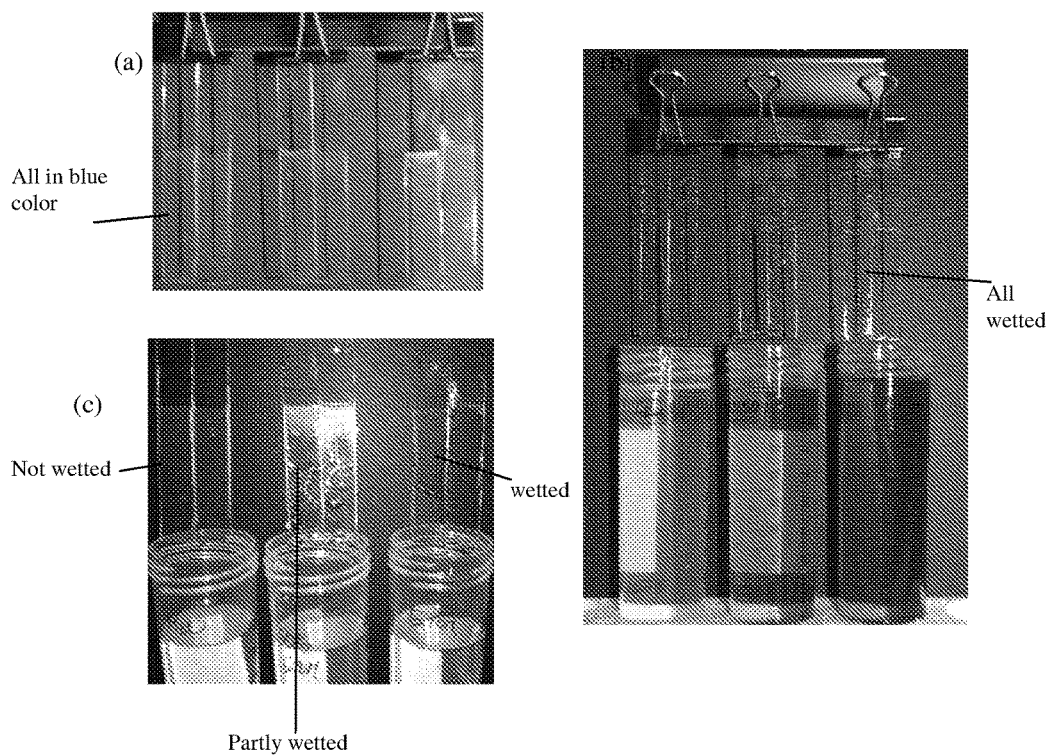
FIG. 12: Test results of three-replicate pairs of silica IOF on quartz. In each set, the left one was coated with 13FS, and the right one was coated with 17 FS. (a) dried IOFs showing pale blue color, (b) Each set of IOF was dipped in gasoline (left), 50:1 gasoline/oil mixture (middle) and 16:1 gasoline/oil mixture (right), and they were all wetted. (c) Each set was dipped in water (left), 50% ethanol (middle), 95% ethanol (right). The IOF were not wetted by water, partly wetted by 50% ethanol, and completely wetted by 95% ethanol.

On Quartz Substrates: Test Results of Silica IOF Prepared by the Evaporation Method Blue-colored silica IOF was also constructed on quartz substrates. Three pairs of silica IOF made on quartz were tested with wetting by liquids (FIG. 12). In each pair, the left strip was coated with 13FS, and the right one was coated with 17 FS. FIG. 12b shows the IOF strips were all wetted by gasoline, the 50:1 and 16:1 gasoline/oil mixtures. On the other hand, the IOF were not wetted by water, partly wetted by 50% ethanol, and completely wetted by 95% ethanol (FIG. 12c), showing the possibility to distinguish between this 3 types of liquids by the IOF strips. Since there was no visual difference between the wetting behaviour of the left and right IOF in each pair, the two silanes used to modify the IOF surfaces didn't provide further information on differentiation.

Figure 13:
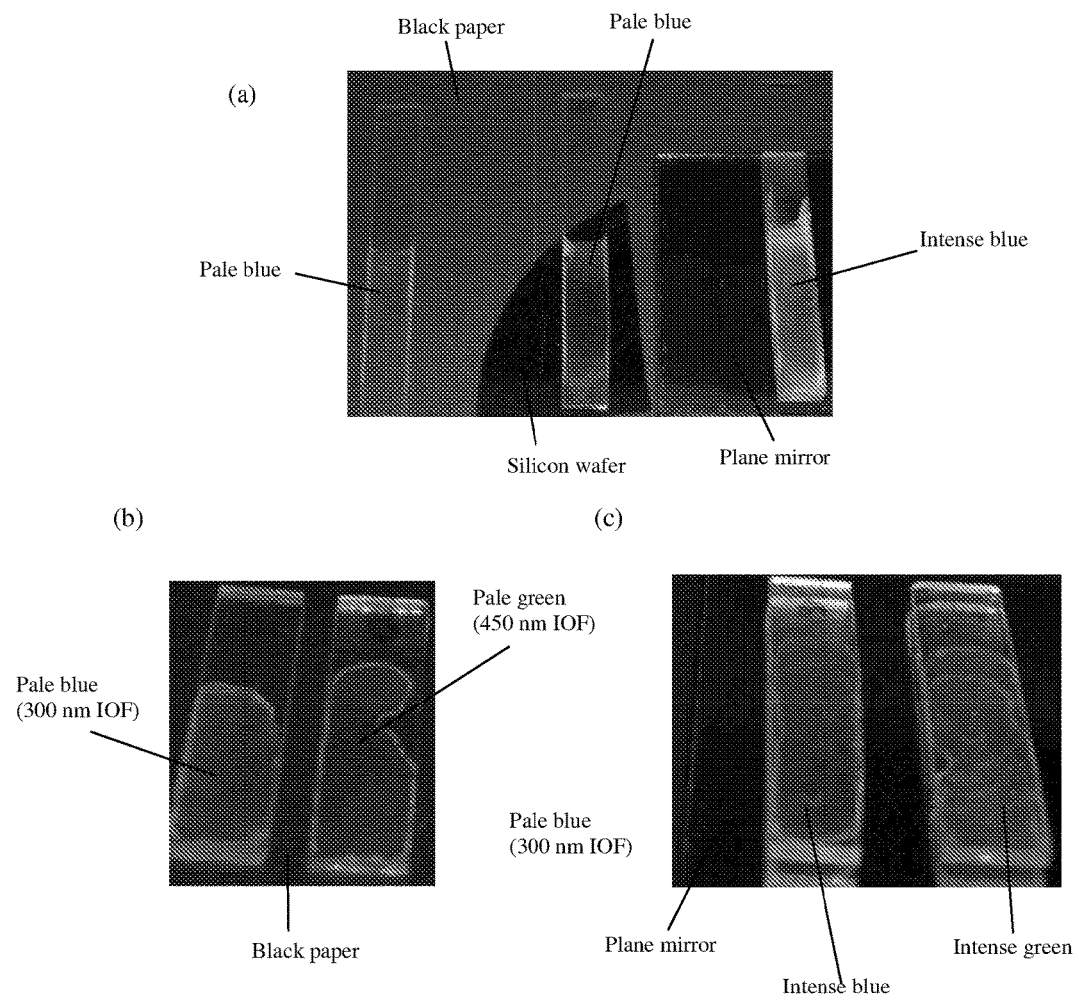
FIG. 13: Contrast of IOF strips made on quartz. (a) The IOFs (300 nm) were placed on black paper (left), silicon wafer (middle), and a mirror (right) for comparison. (b) Two IOFs (the left and right strips were made with 300 and 450 nm PMMA, respectively) were put on black paper. (c) Two IOF strips were put on a mirror.

The contrast of IOF strip made on quartz is not as good as that made on silicon substrate. One reason is the high reflectivity of the silicon as FIG. 13a shows the contrast of the IOF strip on quartz is improved when it is placed on either a mirror or a reflective silicon substrate, as compared to the black paper. Similarly, the contrast of the two IOFs (the left and right were made with 300 and 450 nm PMMA, respectively) put on a mirror (FIG. 13b) was much improved over those put on black paper (FIG. 13c). The IOF strips made of 300 nm PMMA nanospheres shows the usual blue color, whereas the IOF strips made of 450 nm PMMA shows a new yellow-green color because of a different nanopore size.

Zirconia IOF Prepared by the Spotting Method

Zirconia IOF was also synthesized by the spotting method. The difference of refractive index between zirconia and air is expected to be greater than that between silica and air (i.e. $n_{silica}=1.455$, $n_{zirconia}=2.13$, $n_{air}=1$). Therefore, the effect of color disappearance after wetting by various liquids (eg. $n_{gasoline}=1.4$, $n_{oil}=1.475$, $n_{water}=1.333$, $n_{EtOH}=1.36$) will be expected to be greater for zirconia IOF. In this regard, the titania IOF should perform even better as the refractive index of titania is even higher ($n_{titania}=2.50$).

Figure 14:
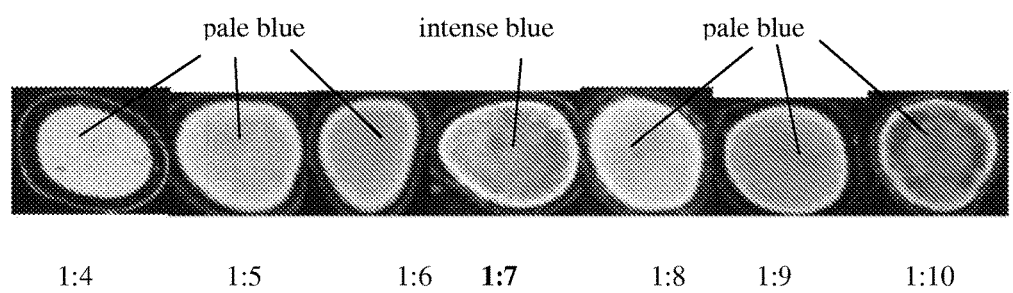
FIG. 14: Synthesis of zirconia IOF by the spotting method using different amounts of methanol. Acidic zirconium acetate of different ratio was prepared by mixing different volume of zirconium acetate with methanol to give a total volume of 10 μL. For instance, the best result was obtained at ratio of 1:7, i.e. 1.3 μL zirconium acetate was mixed with 8.7 μL methanol. In all cases, 1 μL of acidic zirconium acetate was mixed with 9 μL of PMMA colloid.

The conditions for making zirconia IOF were first optimized. Acidic zirconium acetate of different ratios (1:4 to 1:10) was prepared by mixing different volumes of zirconium acetate (solution in dilute acetic acid, 15-16% Zr) with methanol to give a total volume of 10 μL. For instance, the ratio of 1:7 was obtained by mixing 1.3 μL zirconium acetate with 8.7 μL methanol. As shown in FIG. 14, the most intense blue IOF spot was obtained from the ratio of 1:7.

Figure 15:
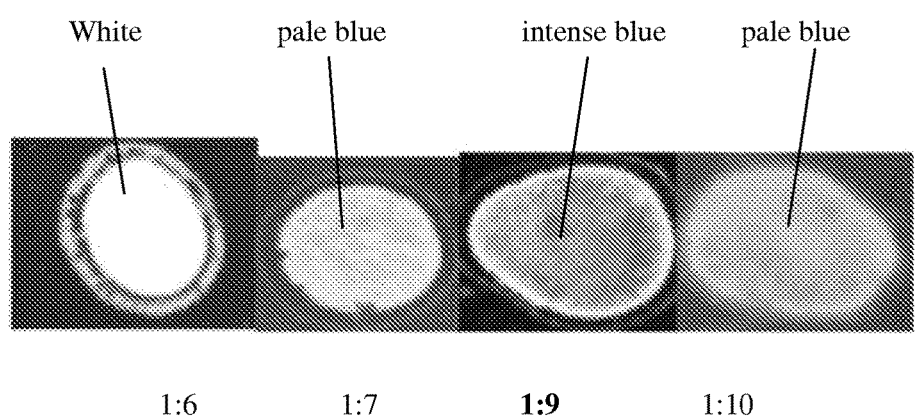
FIG. 15: Synthesis of zirconia IOF by the spotting method using different amounts of PMMA colloid. Different ratios (1:6 to 1:10) of acidic zirconium acetate to the PMMA colloid were investigated. The ratio of 1:9 produced the most intense blue IOF spot color.

Another ratio to optimize is the volume ratio of acidic zirconium acetate and the PMMA colloid. Here, the ratios of 1:6 to 1:10 were investigated. As shown in FIG. 15, the ratio of 1:9 produced the most intense blue color.

Complete Liquid Composition Differentiation

Figure 16:
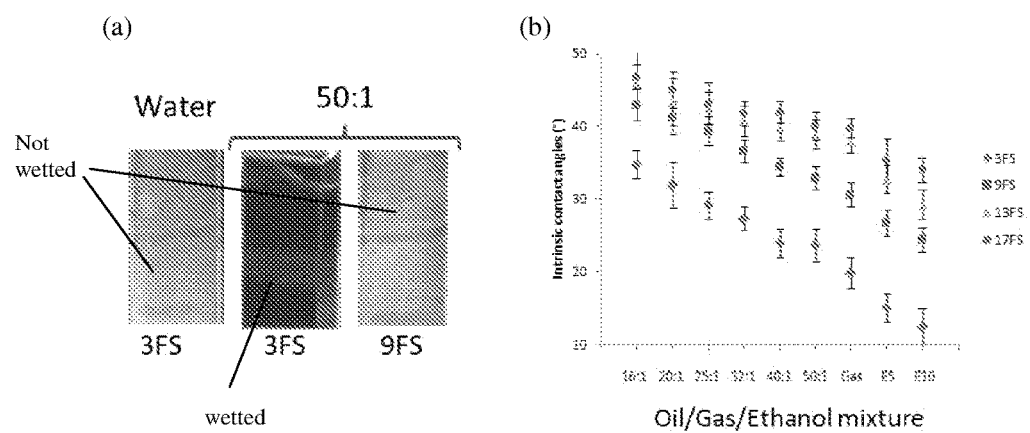
FIG. 16: (a) optical images of an IOF immersed in water and 50:1 solution (a mixture of gasoline/oil with a ratio of 50:1). The IOF silanized with 3FS was wetted by the 50:1 mixture but not by water. After replacement of 3FS with 9FS, the IOF was not wetted even by the 50:1 mixture. (b) the measured contact angles of different gasoline/oil mixtures (16:1, 20:1, 25:1, 32:1, 40:1, 50:1), pure gasoline (gas) and gasoline/ethanol mixtures (E5: 5% ethanol, E10: 10% ethanol) placed on the flat silicon wafer coated with 3FS, 9FS, 13FS and 17FS. The error bars show the standard deviation (SD) of 3 contact angle measurements.

Although the 2 different silanes (13FS and 17FS) did not show different wetting behaviour in FIGS. 12a and b, the use of 3FS and 9FS did. As shown in FIG. 16a, the iridescent color of an IOF coated with a hydrophobic silane (3FS) disappeared as it was immersed in the 50:1 gasoline-to-oil solution, showing the IOF nanopores were wetted. However, if the coating was replaced with 9FS, which had a longer fluoroalkyl chain and hence higher oleophobic property, the nanopores resisted the infiltration by the 50:1 mixture, and the blue color remained. FIG. 16b shows the measured intrinsic contact angle ($\theta_c$) of different gasoline/oil and gasoline/ethanol mixtures on the silicon surfaces coated with silane with different fluoroalkyl chain lengths (and thus different numbers of fluorine atoms in the silane structure). The greater difference of the $\theta_c$ value between 3FS to 9FS explains the difference in the wettability behaviours observed in FIG. 16a. The small difference in the $\theta_c$ values between 13FS and 17FS can explain why there was no difference in the wetting behaviours observed in FIGS. 12b and c. The $\theta_c$ values on all the silane surfaces also decrease as the oil content of the mixtures decreases from 16:1 to 50:1, and even to pure gasoline. This decreasing trend continues (with an even sharper slope of decrease) in the ethanol/gasoline mixtures (E5 and E10). The differences in the measured $\theta_c$ values show the potential for differentiation of the mixtures by tuning the surface chemistry. The small differences (some within experimental errors), however, suggest that relying only on this factor ($\theta_c$ differences) may be inadequate for differentiation of closely-related mixtures that are used in this study. Therefore, other effective factors on tuning the wettability of IOF need to be considered.

Figure 17:
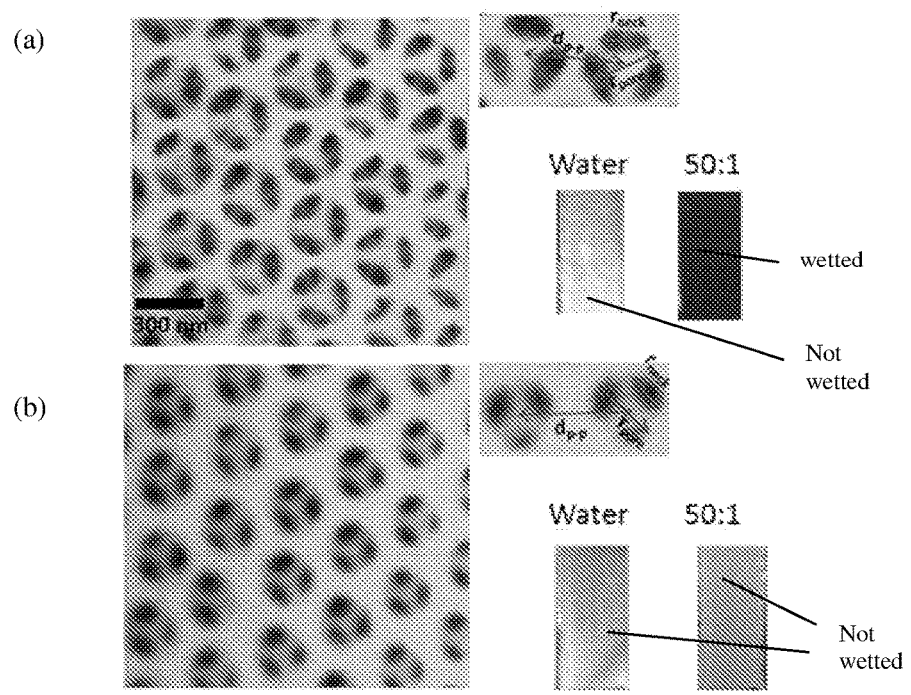
FIG. 17: the SEM images of two different IOFs with different neck angles. Despite the same surface chemistry (both coated with 9FS), different wettability was observed when the IOF was immersed in the 50:1 gasoline/oil mixture. This behaviour is attributed to different neck angle ($\theta_0$) value (sin $\theta_0 = r_{neck}/r_{pore}$). It is defined that $r_{neck}$ is the distance of the neck opening, $r_{pore}$ is the diameter of the pores, and dp-p is the interpore distance. The calculated neck angles for IOF in (a) and (b) are 33±3° and 27±3°, respectively. The smaller neck angle in (b) explains why the IOF is not wetted by the 50:1 mixture, retaining the blue color. The scale bar is 300 nm.

The IOF liquid wettability is also affected by the pore neck angle ($\theta_0$, where $\sin\theta_0 = r_{neck}/r_{pore}$). This angle depends on the neck radius $r_{neck}$ and the pore radius $r_{pore}$. The necks are small openings that connect the IOF pores between layers and through which the fluid fronts propagate from one pore in one layer to the pore in the next, when the IOF is immersed in a liquid. The interpore necks appear as the dark regions in the scanning electron microscopy (SEM) images of the IOF surface (FIG. 17). When a liquid front infiltrates into the pore through the narrow opening of the neck, there are 2 forces in balance with each other: first is the energetically unfavorable liquid-air interfacial force and second is the energetically favorable liquid-solid interfacial force (as long as $\theta_c<90°$). An activation barrier prevent the liquid to fill the pore if $\theta_c$ is larger than the azimuthal (neck) angle ($\theta_c$) [23,25]. The SEM images of two IOFs with different $\theta_0$ values are shown in FIG. 17. The calculated neck angles are 33°±3 and 27°±3 for the IOFs in (a) and (b), respectively. As shown in the optical images of liquid wettability in FIG. 17, the IOFs show different wettabilities even though they have the same surface coating (9FS): the IOF with the neck angle of 33° was wetted by the 50:1 mixture, but the IOF with the neck angle of 27° was not wetted.

The different neck angles can be explained as follows: in the co-assembly procedure to prepare the IOFs, we used the $SiO_2$ sol-gel precursor (TEOS) deposited simultaneously with the PMMA nanospheres [21]. When a colloid is being assembled on an underlying layer, a thin film of precursor interface forms between the assembling colloids and the colloids in the underlying layer (in the co-assembly process, the IOF face-centered cubic lattice grows in the <110> direction of the silicon substrate [21]). At a higher concentration of the precursor, this interface can become thicker and so this decreases the area that collapses to form the neck after thermal decomposition of the polymeric colloids. Therefore a smaller neck size is resulted as the TEOS concentration is enhanced in the co-assembly process, thus giving a useful practical method for tuning the IOF wettability. The TEOS volume used to prepare the IOFs in FIGS. 17a and b are 7.5 and 8.7 μL, respectively. The higher precursor concentration also increases the interpore distance ($d_{p-p}$) and decreases the pore packing ratio (defined as $R_p = r_{pore}/d_{p-p}$), since the higher TEOS concentration also results in thicker walls between the pores in the same layer and therefore a larger spacing between the pores. The pore packing ratio $R_p$ are determined to be 0.84 and 0.72 for the IOFs in FIGS. 17a and b, respectively. A smaller Rp value was the direct result of the increased TEOS concentration, causing the pores to be spaced further apart.

Figure 18:
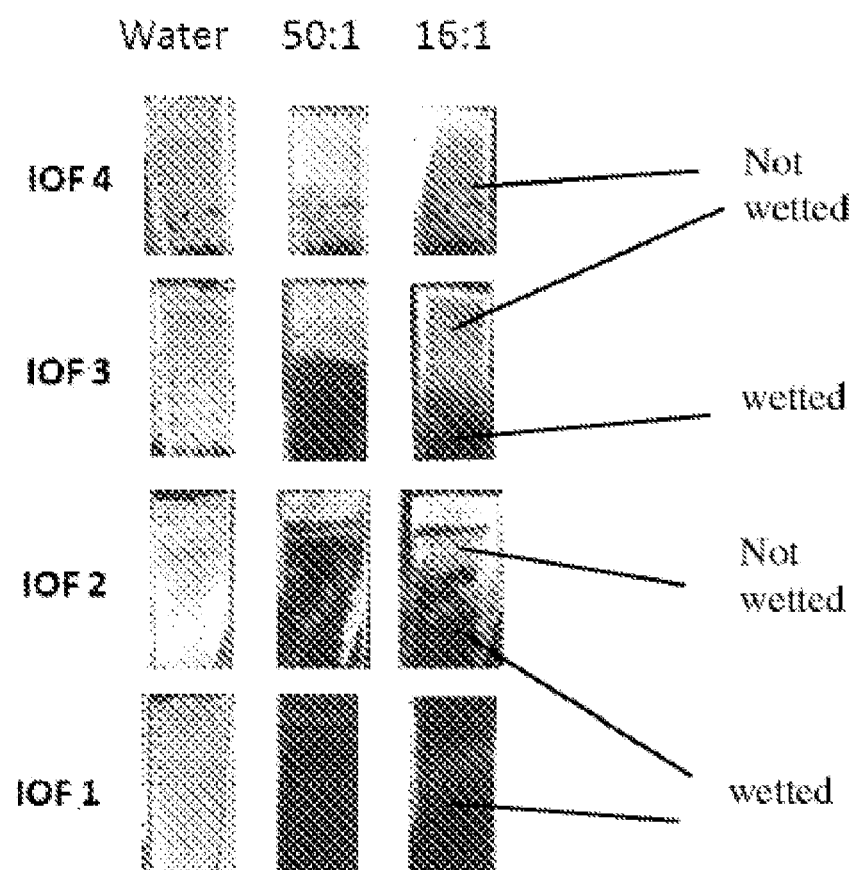
FIG. 18: the optical images of 4 different IOFs, all coated with 3FS, immersed in water, 50:1 and 16:1 gasoline/oil mixtures. Different volumes of the PMMA stock colloid (260, 280, 300 and 320 μL) were each mixed with an identical 25 μL of TEOS, and the mixtures were placed in the film deposition vials in order to prepare IOF1 to 4, respectively.

The thickness of the IOF (i.e. the number of IOF layers) is another factor that affect the IOF wettability. It was showed that the fraction of "filled" pores in each layer decreases with the IOF depth, even if all the IOF surfaces are uniformly coated [23]. This causes the thick IOF to maintain the iridescence color (from the bottom layers), while the color of the thin IOFs disappears as their pores are all filled. The thickness of IOF, synthesized through vertical deposition, is directly proportional to the volume fraction of the colloids in the IOF synthesis solution [26]. Therefore, we tune the IOF thickness by variation of the colloid volume fractions, while keeping a constant TEOS concentration. FIG. 18 shows the wettability results of 4 different IOFs with the same fluorosilane coating (3FS) and TEOS concentration. First, the bottom part of IOF2 and IOF3 were wetted, while the top parts were not. This is due to the increased wettability of a thinner IOF near the bottom, which is attributed to a decreased thickness of the IOF that naturally occurred in vertical deposition [23]. As the colloid volume fraction, i.e. the ratio of PMMA colloid volume to TEOS solution volume, increased from 0.09 in IOF1 to 0.12 in IOF4, the non-wetted area from the bottom to the top increased. In addition, slight mixture differentiations are observed in those IOFs that are partially wetted (IOF 2 and 3), where slightly larger fraction of IOF areas are wetted by the 50:1 mixture (with less oil content) than by the 16:1 mixture (with more oil content). Differentiation of the mixtures can therefore be achieved based on the wetted area fraction, though not in a simple binary wetted/non-wetted manner.

Figure 19:
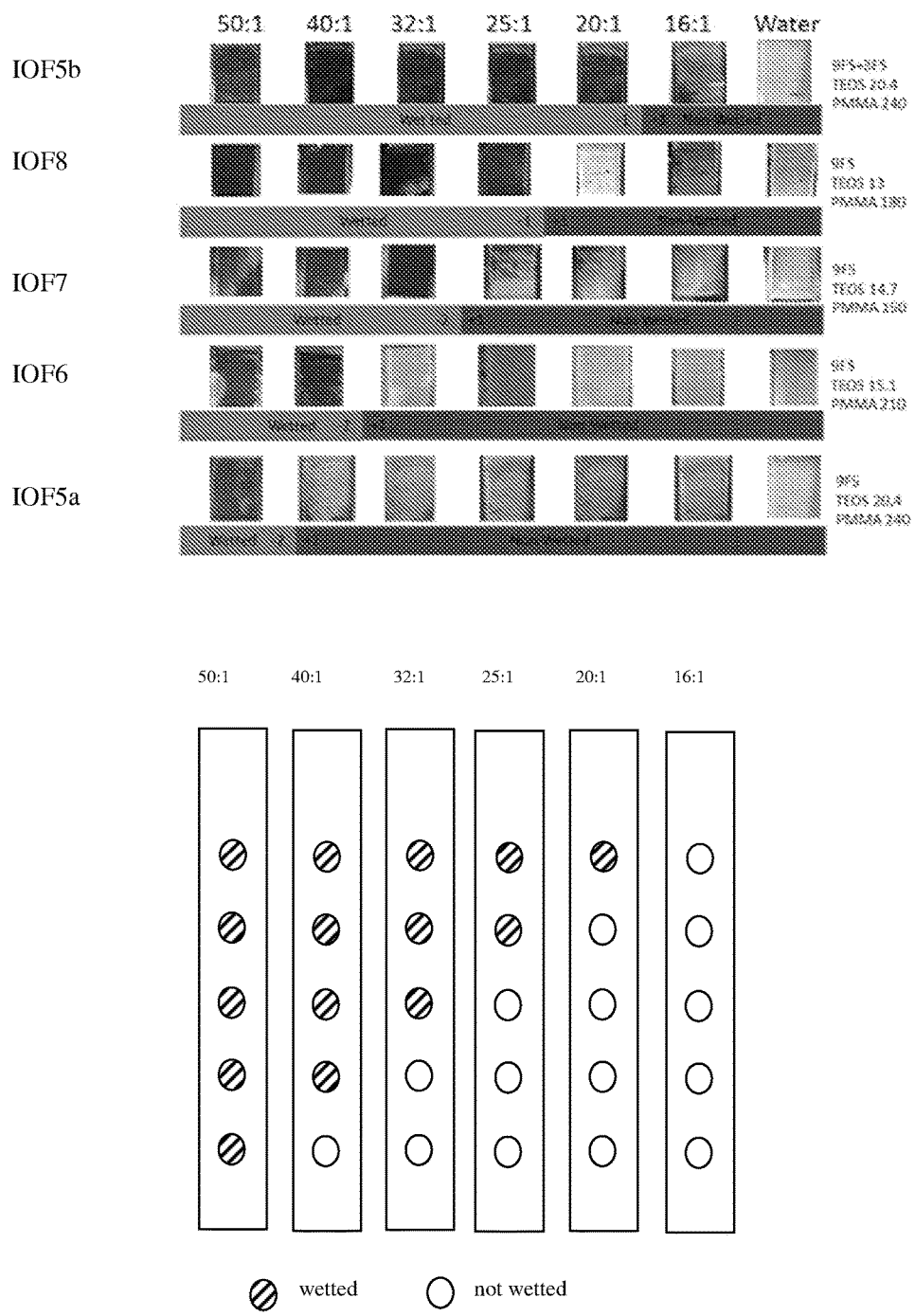
FIG. 19: (a) Test grids of the differentiation of 6 gasoline/oil mixtures. Listed on the right side are the coated silane, TEOS volume and PMMA volume (in μL) used to prepare the IOF; provided on the left side are the IOF codes as tabulated in Table 3. The numbers written on either side of the wettability borders indicates the mixtures with the neighboring nearest mixture ratios that show similar wettability behaviour. The numbers are based on 3 wettability tests performed on different mixtures (table 3). (b) Schematic diagram of six test strips each constructed with five IOFs, and the binary pattern allow us to tell the different among six gasoline/oil mixtures.

In order to prepare a practical colorimetric indicator, several qualities need to be met. The use of the test strip should be simple and straightforward. The results should have adequate sensitivity and reproducibility, and more importantly, easy to read, especially when they are to be read by non-professional users. Here, we aim to prepare IOFs that are capable of differentiation of the liquid mixtures in a binary fashion ("Wetted" vs. "Non-wetted"). Knowing the governing factors on the IOF wettability ($\theta_c$, $\theta_0$ and IOF thickness), as well as the experimental procedures to tune the factors, we prepare different IOFs with a combined variation of these factors. The wettability tests on every IOF are performed in order to find the IOFs with the properties (the values of governing factors) capable of differentiation of a pair of closely related mixtures (e.g. 50:1 and 40:1 mixtures). FIG. 19a shows the optical images of wettability tests on different IOFs capable of differentiating various pairs of gasoline/oil mixtures. Each IOF was wetted by the mixtures down to a certain gasoline:oil ratio and resisted wetting by mixtures with lower ratios, creating a wettability border that differentiated the mixtures on either side of the border. The position of the border among different ratios depends on the values of governing factors, such that $\theta_c$ and IOF thickness are directly, and $\theta_0$ is inversely, proportional to the wettability of the IOF. Interestingly, even the IOF with defected areas (show non-homogeneously wetted regions in the images) were able to selectively differentiate between the mixtures. This is because the IOF selectivity is dictated by the short-range variation (in micrometer scale) rather than long-range variation (in millimeter scale). Although the iridescence color of the IOF is angle-dependent and the visual changes by even slight changes in the viewing angle causes the color change, the differentiation between the non-wetted IOF (colored) and the wetted IOF (display the dark substrate color) is very simple. When these IOFs are incorporated in a test strip, a binary pattern is obvious. For instance, a pattern of wetted IOF5b, wetted IOF8, not wetted IOF7, non-wetted IOF6 and non-wetted IOF5a indicated the mixture to be 25:1±1 (or from 24:1 to 26:1). FIG. 19b shows the schematic diagram of six test strips each constructed with 5 IOFs, and the binary pattern allow us to tell the different among 6 gasoline/oil mixtures. More IOFs can be incorporated in the test strips to increase the resolution of liquid composition differentiation.

Figure 20:
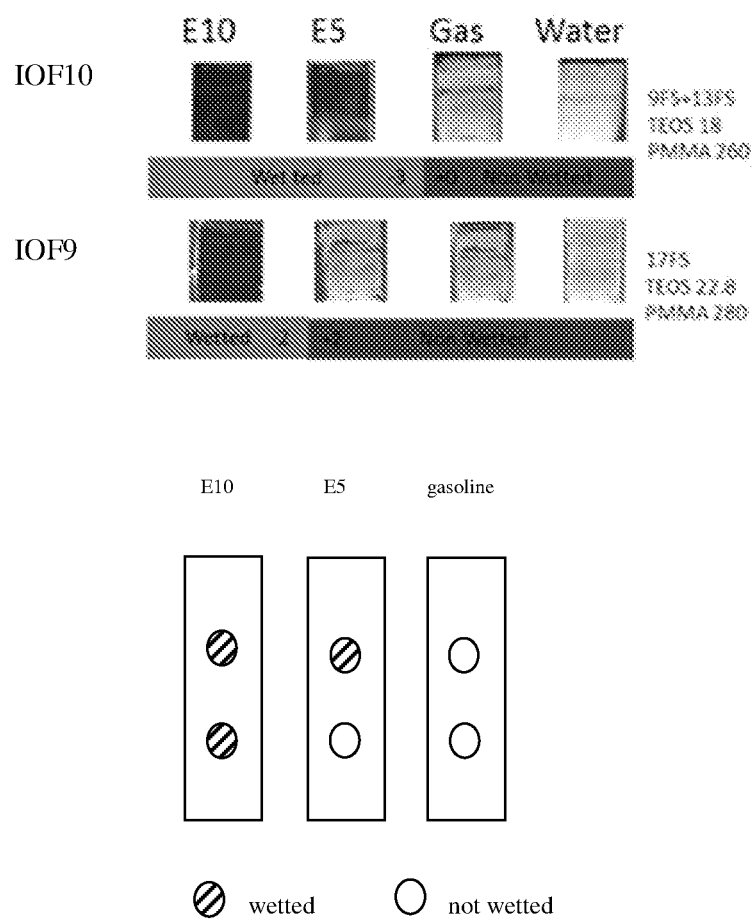
FIG. 20: (a) Test grids showing the optical images of differentiation of the gasoline/ethanol mixtures. Listed on the right side are the coated silane, TEOS volume and PMMA volume (in μL) used to prepare the IOF; provided on the left side are the IOF codes as tabulated in Table 4. The numbers written on either side of the wettability borders indicates the mixtures with the neighboring ratios that show similar wettability behaviour. The numbers are based on 3 wettability tests on different mixtures (table 3). (b) Schematic diagram of three test strips each constructed with two IOFs, and the binary pattern allow us to tell the different among three gasoline/ethanol mixtures.

Similar to the differentiation of gasoline/oil mixture compositions, the test strips were constructed to differentiate between different gasoline/ethanol mixtures. FIG. 20 shows the optical images of wettability tests on different IOFs capable of differentiating various pairs of gasoline/ethanol mixtures (i.e. E10, E5 and pure gasoline). IOF9 was wetted by the E10 mixture but resisted wetting by the E5 mixture, creating a wettability border that differentiated the mixtures on either side of the border. Again, the position of the border among different ratios depends on the values of governing factors, such that $\theta_c$ and IOF thickness are directly, and $\theta_0$ is inversely, proportional to the wettability of the IOF. When these IOFs are incorporated in a test strip, a binary pattern is obvious. FIG. 20b shows the schematic diagram of three test strips each constructed with two IOFs, and the binary pattern allow us to tell the different among three gasoline/ethanol mixtures. More IOFs can be incorporated in the test strips to increase the resolution of liquid composition differentiation.

REFERENCES

1. Bosco J P, Sasaki K, Sadakane M, Ueda W, Chen J G. Synthesis and Characterization of Three-Dimensionally Ordered Macroporous (3DOM) Tungsten Carbide: Application to Direct Methanol Fuel Cells †. *Chem. Mater.* 2010; 22(3):966-973. Available at: http://pubs.acs.org/doi/abs/10.1021/cm901855y. Accessed Dec. 19, 2013.
2. Nishimura S, Abrams N, Lewis B a, et al. Standing wave enhancement of red absorbance and photocurrent in dye-sensitized titanium dioxide photoelectrodes coupled to photonic crystals. *J. Am. Chem. Soc.* 2003; 125(20):6306-10. Available at: http://www.ncbi.nlm.nih.gov/pubmed/12785864.
3. Ke F-S, Huang L, Wei H-B, et al. Fabrication and properties of macroporous tin-cobalt alloy film electrodes for lithium-ion batteries. *J. Power Sources.* 2007; 170(2):450-455. Available at: http://linkinghub.elsevier.com/retrieve/pii/S0378775307006945. Accessed Jan. 3, 2014.
4. Arsenault A C, Clark T J, von Freymann G, et al. From colour fingerprinting to the control of photoluminescence in elastic photonic crystals. *Nat. Mater.* 2006; 5(3):179-184. Available at: http://www.nature.com/doifinder/10.1038/nmat1588. Accessed Dec. 17, 2013.
5. Blanco a, Chomski E, Grabtchak S, et al. Large-scale synthesis of a silicon photonic crystal with a complete three-dimensional bandgap near 1.5 micrometers. *Nature.* 2000; 405(6785):437-40. Available at: http://www.ncbi.nlm.nih.gov/pubmed/10839534.
6. 1. Chen J I L, von Freymann G, Choi S Y, Kitaev V, Ozin G a. Slow photons in the fast lane in chemistry. *J. Mater. Chem.* 2008; 18(4):369. Available at: http://xlink.rsc.org/?DOI=b708474a. Accessed Jan. 4, 2014.
7. 1. Wei Y, Liu J, Zhao Z, Duan A, Jiang G. The catalysts of three-dimensionally ordered macroporous Ce1-xZrxO2-supported gold nanoparticles for soot combustion: The metal-support interaction. *J. Catal.* 2012; 287:13-29.

Available at: http://linkinghub.elsevier.com/retrieve/pii/S0021951711003678. Accessed Jan. 4, 2014.
8. 1. Guan G. Preferential CO oxidation over catalysts with well-defined inverse opal structure in microchannels. *Int. J. Hydrogen Energy.* 2008; 33(2):797-801. Available at: http://linkinghub.elsevier.com/retrieve/pii/S0360319907006787. Accessed Dec. 17, 2013.
9. 1. Xu M, Feng D, Dai R, Wu H, Zhao D, Zheng G. Synthesis of hierarchically nanoporous silica films for controlled drug loading and release. *Nanoscale.* 2011; 3(8):3329-33. Available at: http://www.ncbi.nlm.nih.gov/pubmed/21717013. Accessed Jan. 4, 2014.
10. 1. Bai Y, Yang W, Sun Y, Sun C. Enzyme-free glucose sensor based on a three-dimensional gold film electrode. *Sensors Actuators B Chem.* 2008; 134(2):471-476. Available at: http://linkinghub.elsevier.com/retrieve/pii/S0925400508003729. Accessed Dec. 12, 2013.
11. 1. Stein A, Wilson B E, Rudisill S G. Design and functionality of colloidal-crystal-templated materials—chemical applications of inverse opals. *Chem. Soc. Rev.* 2013; 42(7):2763-803. Available at: http://www.ncbi.nlm.nih.gov/pubmed/23079696. Accessed Jun. 14, 2013.
12. 1. Nishijima Y, Ueno K, Juodkazis S, et al. Inverse silica opal photonic crystals for optical sensing applications. *Opt. Express.* 2007; 15(20):12979-88. Available at: http://www.ncbi.nlm.nih.gov/pubmed/19550567.
13. 1. Khunsin W, Romanov S G, Scharrer M, Aagesen L K, Chang R P H, Sotomayor Torres C M. Chemosorption-related shift of a photonic bandgap in photoconductive ZnO inverse opal. *Opt. Lett.* 2008; 33(5):461-3. Available at: http://www.ncbi.nlm.nih.gov/pubmed/18311292.
14. 1. Liu Z, Xie Z, Zhao X, Gu Z-Z. Stretched photonic suspension array for label-free high-throughput assay. *J. Mater. Chem.* 2008; 18(28):3309. Available at: http://xlink.rsc.org/?DOI=b807732k. Accessed Jan. 4, 2014.
15. 1. Li H, Chang L, Wang J, Yang L, Song Y. A colorful oil-sensitive carbon inverse opal. *J. Mater. Chem.* 2008; 18(42):5098. Available at: http://xlink.rsc.org/?DOI=b808675c. Accessed Dec. 24, 2013.
16. 1. Song Y-Y, Zhang D, Gao W, Xia X-H. Nonenzymatic glucose detection by using a three-dimensionally ordered, macroporous platinum template. *Chemistry.* 2005; 11(7):2177-82. Available at: http://www.ncbi.nlm.nih.gov/pubmed/15714534. Accessed Jan. 4, 2014.
17. 1. Zhou J, Huang H, Xuan J, Zhang J, Zhu J-J. Quantum dots electrochemical aptasensor based on three-dimensionally ordered macroporous gold film for the detection of ATP. *Biosens. Bioelectron.* 2010; 26(2):834-40. Available at: http://www.ncbi.nlm.nih.gov/pubmed/20886696. Accessed Jan. 4, 2014.
18. 1. Burgess I B, Lončar M, Aizenberg J. Structural colour in colourimetric sensors and indicators. *J. Mater. Chem. C.* 2013; 1(38):6075. Available at: http://xlink.rsc.org/?DOI=c3tc30919c. Accessed Jan. 2, 2014.
19. 1. Meseguer F, Blanco A, M$_1$ H. Synthesis of inverse opals. *Colloids Surf, A* 2002; 202:281-290.
20. 1. Wei H, Meng L, Jun Y, Norris D J. Quantifying stacking faults and vacancies in thin convectively assembled colloidal crystals. *Appl. Phys. Lett.* 2006; 89(24):241913. Available at: http://link.aip.org/link/APPLAB/v89/i24/p241913/s1&Agg=doi. Accessed Jan. 4, 2014.
21. 1. Hatton B, Mishchenko L, Davis S, Sandhage K H, Aizenberg J. Assembly of large-area, highly ordered, crack-free inverse opal films. *Proc. Natl. Acad. Sci. U.S.A.* 2010; 107(23):10354-9. Available at: http://www.pubmedcentral.nih.gov/articlerender.fcgi?artid=2890797&tool=pmcentrez&rendertype=abstract. Accessed May 29, 2013.
22. 1. Burgess I B, Mishchenko L, Hatton B D, Kolle M, Lon M, Aizenberg J. Encoding Complex Wettability Patterns in Chemically Functionalized. *J. Am. Chem. Soc.* 2011: 12430-12432.
23. 1. Burgess I B, Koay N, Raymond K P, Kolle M, Lončar M, Aizenberg J. Wetting in color: colorimetric differentiation of organic liquids with high selectivity. *ACS Nano.* 2012; 6(2):1427-37. Available at: http://www.ncbi.nlm.nih.gov/pubmed/22185377.
24. 1. Raymond K P, Burgess I B, Kinney M H, Lončar M, Aizenberg J. Combinatorial wetting in colour: an optofluidic nose. *Lab Chip.* 2012; 12(19):3666-9. Available at: http://www.ncbi.nlm.nih.gov/pubmed/22773181. Accessed Jun. 26, 2013.
25. 1. Tuteja A, Choi W, Mabry J M, McKinley G H, Cohen R E. Robust omniphobic surfaces. *Proc. Natl. Acad. Sci. U.S.A.* 2008; 105(47):18200-5. Available at: http://www.pubmedcentral.nih.gov/articlerender.fcgi?artid=2587612&tool=pmcentrez&rendertype=abstract.
26. 1. Jiang P, Bertone J F, Hwang K S, Colvin V L. Single-Crystal Colloidal Multilayers of Controlled Thickness. 1999; (25):2132-2140.

TABLE 1

The name and abbreviation of the silanes used in silanization of IOF.

| Name | Abbreviation |
| --- | --- |
| 3-aminopropyltriethoxysilane | APTES |
| Chlorotrimethylsilane | TMS |
| Chlorotriphenylsilane | TPS |
| Dimethyldichlorosilane | RS |
| Trichloro(hexyl)silane | C6 |
| Chloro(dimethyl)octadecylsilane | C18 |
| 3,3,3-trifluoropropyltrichlorosilane | 3FS |
| Nonafluorohexyltrichlorosilane | 9FS |
| (1H,1H,2H,2H-perfluorooctyl)trichlorosilane | 13FS |
| Heptadecafluoro (1,1,2,2-tetrahydrodecyl)trichlorosilane | 17FS |
| Perfluorododecyl(1H,1H,2H,2H-)triethoxysilane | 25FS |

TABLE 2

Result of the wettability tests of 8 kinds of liquids on IOF coated with 7 types of silanes (for abbreviations of the silanes used, see Table 1)

| Silane | Water | EtOH 95% | Toluene | Gasoline | 50:1 | 40:1 | 1:1 | Oil |
| --- | --- | --- | --- | --- | --- | --- | --- | --- |
| APTES | N | W | W | W | — | — | — | W |
| TMS | N | W | W | W | — | — | — | W |
| RS | N | W | W | W | — | W | — | N |
| C6 | N | W | W | W | — | — | — | W |
| C18 | N | W | W | W | — | — | — | W |
| 3FS | N | W | W | W | — | W | — | W |
| 13FS | N | W | W | W | W | N | N | N |

Liquid wetted and removed the blue color on the spot (W),
Liquid did not wet or remove the blue color on the spot (NW),
did not test (—)

TABLE 3

Result of wettability tests of gasoline/oil mixtures. The symbols "W", "N" and "ND" mean that the IOF is wetted, non-wetted or non-distinguishable wettability, respectively. The term NRM defines the interval that shows similar wettability as the main ratio composition according to the wettability tests.

| code | Mixture | Trial 1 | Trial 2 | Trial 3 | NRM |
|---|---|---|---|---|---|
| IOF5b | 50:1 | W | W | W | |
| | 48:1 | W | W | W | −2 |
| | 46:1 | W | ND | N | |
| | 44:1 | N | W | ND | |
| | 42:1 | N | N | N | |
| | 40:1 | N | N | N | +2 |
| IOF8 | 40:1 | W | W | W | |
| | 38:1 | W | W | W | −2 |
| | 36:1 | ND | W | ND | |
| | 34:1 | N | W | N | |
| | 33:1 | N | N | N | |
| | 32:1 | N | N | N | +1 |
| IOF7 | 32:1 | W | W | W | |
| | 30:1 | W | W | W | −2 |
| | 28:1 | N | N | ND | |
| | 26:1 | N | N | N | |
| | 25:1 | N | N | N | +1 |
| IOF6 | 25:1 | W | W | W | |
| | 24:1 | W | W | W | −1 |
| | 23:1 | W | W | N | |
| | 22:1 | ND | N | ND | |
| | 21:1 | N | N | N | |
| | 20:1 | N | N | N | +1 |
| IOF5a | 20:1 | W | W | W | |
| | 19:1 | W | W | W | −1 |
| | 18:1 | W | ND | N | |
| | 17:1 | N | N | N | |
| | 16:1 | N | N | N | |

NRM: nearest-ratio mixtures that are wetted
ND: Non-distinguishable
W: Wetted
N: Non-Wetted

TABLE 4

Result of wettability tests of gasoline/ethanol mixtures. The symbols "W", "N" and "ND" mean that the IOF is wetted, non-wetted or non-distinguishable wettability, respectively. The term NRM defines the interval that shows similar wettability as the main ratio composition according to the wettability tests.

| code | Mixture | Trial 1 | Trial 2 | trial 3 | NRM |
|---|---|---|---|---|---|
| IOF10 | E10 | W | W | W | |
| | E9 | W | W | W | −2 |
| | E8 | W | W | W | |
| | E7 | N | N | W | |
| | E6 | N | N | N | +2 |
| | E5 | N | N | N | |
| IOF9 | E5 | W | W | W | |
| | E4 | W | W | W | −3 |
| | E3 | W | W | W | |
| | E2 | W | W | W | |
| | E1 | N | N | W | |
| | Gas | N | N | N | +0 |

NRM: nearest-ratio mixtures that are wetted
ND: Non-distinguishable
W: Wetted
N: Non-Wetted While the preferred and additional alternative embodiments of the invention have been illustrated and described, it will be appreciated that various changes can be made therein without departing from the spirit and scope of the invention. Therefore, it will be appreciated that various changes can be made therein without departing from the spirit and scope of the invention. Accordingly, the inventors make the following claims.

What is claimed is:

1. A test strip, comprising:
a first substrate;
at least one inverse opal film deposited on the first substrate, said inverse opal film having a specific neck angle for tuning the wettability of said inverse opal film;
at least one chemical coating deposited inside the pores of the at least one inverse opal film;
said inverse opal film having a specific thickness;
wherein the neck angle, the chemical coating and the thickness of said inverse opal film are optimized such that the neck angle is determined by adjusting template-filler agent ratios in a range of 5.2 to 12.3 and the thickness of said inverse opal film is determined by adjusting colloid volume fractions in a range of 0.05 v % to 0.12 v % and said inverse opal film has the characteristic of being able to be wetted or non-wetted in a binary fashion in relation to a pair of liquid compositions, the liquid compositions having a gasoline concentration of at least 80%, wherein said inverse opal film is wetted when immersed in a first one of the pair of liquid compositions, but is non-wetted when immersed in a second one of the pair of liquid compositions;
and wherein the pair of liquid compositions is selected from the group of gasoline and engine oil mixtures, the ratio of gasoline to engine oil being 50:1, 40:1, 32:1, 25:1, 20:1 and 16:1, or the group of gasoline and ethanol mixtures, the ratio of gasoline to ethanol being 95:5, 90:10 and 85:15, and gasoline containing 0% ethanol.

2. The test strip of claim 1, wherein the first substrate is silicon, quartz, or glass.

3. The test strip of claim 1, wherein the inverse opal film is made of silica, zirconia or titania.

4. The test strip of claim 1, wherein the chemical coating is a silane.

5. The test strip of claim 4, wherein the silane is a fluorosilane.

6. The test strip of claim 4, wherein the silane is one of 3-aminopropyltriethoxysilane, chlorotrimethylsilane, chlorotriphenylsilane, dimethyldichlorosilane, trichloro(hexyl)silane, chloro(dimethyl)octadecylsilane, 3,3,3-trifluoropropyltrichlorosilane, nonafluorohexyltrichlorosilane, heptadecafluoro (1,1,2,2-tetrahydrodecyl)trichlorosilane, and perfluorododecyl(1H,1H,2H,2H-) triethoxysilane.

7. A test strip, comprising:
a first substrate;
at least one second substrate mounted on the first substrate;
at least one inverse opal film deposited on the at least one second substrate, said inverse opal film having a specific neck angle for tuning the wettability of said inverse opal film;
and
at least one chemical coating deposited in the pores of the at least one inverse opal film;
said inverse opal film having a specific thickness;
wherein the neck angle, the chemical coating and the thickness of said inverse opal film are optimized such that the neck angle is determined by adjusting template-filler agent ratios in a range of 5.2 to 12.3 and the thickness of said inverse opal film is determined by adjusting colloid volume fractions in a range of 0.05 v % to 0.12 v % and said inverse opal film has the characteristic of being able to be wetted or non-wetted in a binary fashion in relation to a pair of liquid compositions, the liquid compositions having a gasoline concentration of at least 80%, wherein said inverse opal film is wetted when immersed in a first one of the pair of liquid compositions, but is non-wetted when immersed in a second one of the pair of liquid compositions;

and wherein the pair of liquid compositions is selected from the group of gasoline and engine oil mixtures, the ratio of gasoline to engine oil being 50:1, 40:1, 32:1, 25:1, 20:1 and 16:1, or the group of gasoline and ethanol mixtures, the ratio of gasoline to ethanol being 95:5, 90:10 and 85:15, and gasoline containing 0% ethanol.

8. The test strip of claim 7, wherein the first substrate is silicon, quartz, glass, plastic or paper.

9. The test strip of claim 7, wherein the second substrate is silicon, quartz, or glass.

10. The test strip of claim 7, wherein the inverse opal film is made of silica, zirconia or titania.

11. The test strip of claim 7, wherein the chemical coating is a silane.

12. The test strip of claim 11, wherein the silane is a fluorosilane.

13. The test strip of claim 11, wherein the silane is one of 3-aminopropyltriethoxysilane, chlorotrimethylsilane, chlorotriphenylsilane, dimethyldichlorosilane, trichloro(hexyl)silane, chloro(dimethyl)octadecylsilane, 3,3,3-trifluoropropyltrichlorosilane, nonafluorohexyltrichlorosilane, heptadecafluoro (1,1,2,2-tetrahydrodecyl)trichlorosilane, and perfluorododecyl(1H,1H,2H,2H-) triethoxysilane.

14. The test strip of claim 1, wherein said inverse opal film is synthesized in a process comprising the steps of (a) forming a colloid comprising template nanoparticles and a matrix precursor, (b) applying the colloid to a surface of the first substrate, (c) decomposing the template nanoparticles to leave behind nanopores, thereby forming said inverse opal film, and wherein the concentration of the matrix precursor in the colloid or the ratio of the matrix precursor to the template nanoparticles in the colloid is specifically selected to result in said inverse opal film having said specific neck angle.

15. The test strip of claim 7, wherein the test strip comprises at least five inverse opal films, wherein the first inverse opal film is capable of differentiating between 50:1 and 40:1 gasoline/engine oil mixtures, the second inverse opal film is capable of differentiating between 40:1 and 32:1 gasoline/engine oil mixtures, the third inverse opal film is capable of differentiating between 32:1 and 25:1 gasoline/engine oil mixtures, the fourth inverse opal film is capable of differentiating between 25:1 and 20:1 gasoline/engine oil mixtures, and the fifth inverse opal film is capable of differentiating between 20:1 and 16:1 gasoline/engine oil mixtures.

16. The test strip of claim 7, wherein the test strip comprises at least two inverse opal films, wherein the first inverse opal film is capable of differentiating between gasoline containing 0% ethanol and 95:5 gasoline/ethanol mixture, and the second inverse opal film is capable of differentiating between 95:5 and 90:10 gasoline/ethanol mixtures.

17. A method of determining the concentration of engine oil in a gasoline/engine oil mixture sample, the method comprising:
(a) providing the test strip according to claim 15;
(b) immersing the test strip in a gasoline/engine oil mixture sample; and
(c) monitoring if one or more of the inverse opal films are wetted by the sample.

18. A method of determining the concentration of ethanol in a gasoline/ethanol mixture, the method comprising:
(a) providing the test strip according to claim 16;
(b) immersing the test strip in a gasoline/ethanol mixture sample; and
(c) monitoring if one or more of the inverse opal films are wetted by the sample.

19. The test strip of claim 1, wherein the inverse opal film is made of zirconia or titania.

20. A test strip, comprising:
a first substrate;
at least one inverse opal film deposited on the first substrate, said inverse opal film having a specific neck angle for tuning the wettability of said inverse opal film;
at least one chemical coating deposited inside the pores of the at least one inverse opal film;
said inverse opal film having a specific thickness;
wherein the neck angle, the chemical coating and the thickness of said inverse opal film are optimized such that the neck angle is determined by adjusting template-filler agent ratios in a range of 5.2 to 12.3 and the thickness of said inverse opal film is determined by adjusting colloid volume fractions in a range of 0.05 v % to 0.12 v % and said inverse opal film has the characteristic of being able to be wetted or non-wetted in a binary fashion in relation to a pair of liquid compositions, the liquid compositions having a gasoline concentration of at least 80%, wherein said inverse opal film is wetted when immersed in a first one of the pair of liquid compositions, but is non-wetted when immersed in a second one of the pair of liquid compositions.

* * * * *